United States Patent
Chen et al.

(10) Patent No.: US 7,531,649 B2
(45) Date of Patent: May 12, 2009

(54) APTAMERS TO HUMAN EPIDERMAL GROWTH FACTOR RECEPTOR-3

(75) Inventors: Chi-Hong B. Chen, Los Angeles, CA (US); Ralf Landgraf, Van Nuys, CA (US)

(73) Assignee: The Regents of the University of California, Oakland, CA (US)

(*) Notice: Subject to any disclaimer, the term of this patent is extended or adjusted under 35 U.S.C. 154(b) by 155 days.

(21) Appl. No.: 10/563,888

(22) PCT Filed: Jul. 16, 2004

(86) PCT No.: PCT/US2004/023039

§ 371 (c)(1), (2), (4) Date: Jan. 9, 2006

(87) PCT Pub. No.: WO2005/040339

PCT Pub. Date: Jun. 5, 2005

(65) Prior Publication Data

US 2007/0027096 A1    Feb. 1, 2007

Related U.S. Application Data

(60) Provisional application No. 60/488,679, filed on Jul. 18, 2003.

(51) Int. Cl.
  *C07H 21/04* (2006.01)
  *C12Q 1/68* (2006.01)
  *C12N 15/00* (2006.01)
  *A61K 31/70* (2006.01)

(52) U.S. Cl. .................. 536/24.5; 536/23.1; 435/6; 435/320.1; 514/44

(58) Field of Classification Search .............. None
See application file for complete search history.

(56) References Cited

OTHER PUBLICATIONS

Opalinska et al. Nature Reviews Drug Discovery, 2002, vol. 1, p. 503-514.*
Gullick "The c-erbB3/HER3 receptor in human cancer," Cancer Surveys 1996, vol. 37, pp. 339.349.
Chen et al., "Inhibition of heregulin signaling by an aptamer that preferentially binds to oligomeric form of human epiderman growth factor receptor-3," Proceedings of the National Academy of Sciences of the USA, Aug. 2003, vol. 100, No. 16, pp. 9226-9231.

* cited by examiner

*Primary Examiner*—Tracy Vivlemore
(74) *Attorney, Agent, or Firm*—Gates & Cooper LLP

(57) ABSTRACT

The disclosure provided herein provides compositions of nucleic acid aptamers that bind human epidermal growth factor receptor-3 and methods for their use.

19 Claims, 11 Drawing Sheets

FIG. 1

T7 Promoter    EcoR1    random    BamH1

TAATACGACTCACTATAGGGAATTCCGCGTGTGC — 49nt — GTCCGTTCGGGATCCTC

A6    AGAACAAUCGCAUAGGCCGCAAGGUUAGUUCGUUGUCCGCCGUGCA
A18   ACGAGUAUAGCCCACAUGGCACGACAGGGACGUUUCAUGUGCACAGUUG
A19   AGAUCAGGACACAGAGAGGCCACAGGUGCCAUCCUGGUCUAACGCCUCGAUG
A23   GAGGGCGAGGAGGAGCGCGAGUAUAGCCCUAGAGGUGGAUGUUUCACGGU
A30   CAGGCGAAAGUUGGCGUAUGGGUCACAUCGCAGGCACAUGUCAUCGGGCG
A37   UUGAGAGGUCGUGCCAACUCUCAAGGUUGUUUGCUCUCCGCUCUGUG

5'-TAATACGACTCACTATAGGGAATTCCGCGTGTGCCAGCGAAAGUUGCGUAUGGGUCACAUCGCAGGCACAUGUCAUCUGGGCGGUCCGUUCGGGATCCTC-3'

5'-GGAAUUCCGCGUGUGCCAGCGAAAGUUGCGUAUGGGUCACAUCGCAGGCACAUGUCAUCUGGGGCGGUCCGUUCGGGAU-3'

5'-CAGCGAAAGUUGCGUAUGGGUCACAUCGCAGGCACAUGUCAUCUGGGCGGG-3'

5'-CAGCGAAAGUUGCGUAUGGGUCACAUCGCAGGCACAUGUCAUCUGGGCG-3'

5'-GGGUGCCAGCGAAAGUUGCGUAUGGGUCACAUCGCAGGCACCC-3'

5'-CAGCGAAAGUUGCGUAUGGGUCACAUCGCAGGCAC-3'
A30 COMMON SEQUENCE

5'-CAGCGAAAGUUGCGUAUGGGUCACAUCGCAG-3'
A30 TRIPLE LOOP SEQUENCE

FIG. 9

APTAMERS TO HUMAN EPIDERMAL GROWTH FACTOR RECEPTOR-3

CROSS-REFERENCE TO RELATED APPLICATIONS

This application is a national stage filing of PCT/US04/23039, filed Jul. 16, 2004, which claims priority to U.S. Provisional Application Ser. No. 60/488,679 filed Jul. 18, 2003, the contents of which are incorporated herein by reference.

STATEMENT OF GOVERNMENT SUPPORT

This invention was made in part with United States government support under National Institutes of Health Grant No. GM-21199. The Government has certain rights in the invention.

FIELD OF THE INVENTION

The present invention provides compositions of nucleic acid aptamers that bind human epidermal growth factor receptor-3 and methods for their use.

BACKGROUND OF THE INVENTION

Receptor tyrosine kinases (RTKs) are involved in a broad spectrum of cell growth and differentiation events. RTKs are classified based on sequence homology and domain organization. Type I RTKs include the epithelial growth factor receptor (EGFR) and the Human EGF Receptor homologues HER2 (HER2/neu, p185), HER3 and HER4 (also named c-erbB1-4). Overexpression of several members of this receptor family, especially EGFR and HER2, is associated with a variety of solid tumor malignancies (see, e.g. Dougall et al. (1993) J Cell Biochem 53, 61-73; Berchuck et al. (1990) Cancer Res 50, 4087-91; Schneider et al. (1989) Cancer Res 49, 4968-71; Yokota et al. (1988) Oncogene 2, 283-7; and Slamon et al. (1989) Science 244, 707-12). Overexpression of HER2 is found in 20-30% of breast cancers and results in ligand independent activation and more aggressive growth behavior (see, e.g. Slamon et al. (1989) Science 244,707-12).

Among the four mammalian type I RTKs, HER3 is unique because of its catalytically deficient kinase domain (see, e.g. Guy et al. (1994) Proc Natl Acad Sci USA 91, 8132-6), its high propensity to self-associate in the absence of ligand (see, e.g. Landgraf et al. (2000) Biochemistry 39, 8503-8511) and the ability of the monomeric species of HER3ECD to assume a locked conformation, using an intramolecular tether (see, e.g. Cho et al. (2002) Science 297, 1330-3). HER3 binds a variety of isoforms of the EGF homolog heregulin, and signaling relies on heterodimerization with other RTKs, preferentially HER2 (see, e.g. Sliwkowski et al. (1994) Journal of Biological Chemistry 269, 14661-5). HER2 has a potent cytoplasmic kinase domain but is deficient in ligand binding. Simultaneous overexpression of both HER2 and HER3 is found in several cancers (see, e.g. see, e.g. Naidu et al. (1998) Br J Cancer 78, 1385-90; and Krahn et al. (2001) Eur J Cancer 37, 251-9), and the increased drug resistance in many HER2 overexpressing cancers depends on increased levels of HER3 or EGFR (see, e.g. Chen et al. (2000) Biochem Biophys Res Commun 277, 757-63).

Ligand controlled signaling by type I RTKs involves receptor dimers. However, at elevated expression levels HER2 and other RTKs are likely to be engaged in a broader range of interactions. Activation of HER2 has been shown to result in the formation of large clusters of activated receptors from preexisting smaller clusters (see, e.g. Nagy et al. (1999) J Cell Sci 112 (Pt 11), 1733-41). For EGFR, ligand-independent interactions of receptors have been implicated in the rapid spread of signal over the entire surface of the cell after localized stimulation with immobilized ligand (see, e.g. Verveer et al. (2000) Science 290, 1567-70).

The extracellular domains of RTKs (ECDs) provide attractive targets for macromolecular anti-cancer drugs. Examples include soluble ECDs of the receptors (see, e.g. Azios et al. (2001) Oncogene 20, 5199-209) and antibodies against the ECDs (see, e.g. Ranson et al. (2002) Oncology 63 Suppl 1, 17-24; and Agus et al. (2002) Cancer Cell 2, 127-37). Herceptin, a humanized antibody against HER2, has shown great promise in the treatment of HER2 overexpressing breast cancers (see, e.g. Pegram et al. (1999) Oncogene 18, 2241-51), thus demonstrating two important points. First, interference by large macromolecules with this first level of the signaling cascade holds therapeutic potential. Second, intrinsic toxicity is not required for a drug to be effective against cells that overexpress growth factor receptors.

As macromolecular drugs, RNA aptamers against RTKs have advantages over proteins. Libraries of randomized RNAs can be generated in vitro with a very high level of sequence complexity. Libraries can be screened in vitro using SELEX (Systematic Evolution of Ligands by EXponential enrichment) (see, e.g. Gold et al. (1995) Annu Rev Biochem 64, 763-97). A variety of chemical modifications exists for nucleic acids, such as the incorporation of radiolabels, fluorescent probes, or cross-linking reagents, and modifications to the backbone or specific bases can be introduced at will, thereby adding functionality and stability. RNA aptamers are non-immunogenic, and the use of fluorine or amino groups in the 2' position significantly enhances the half-life of RNA-aptamers in serum.

In recent years, aptamers have been selected successfully against several extracellular protein ligands, such as TGFβ, PDGF, basic FGF and VEGF (see, e.g. Golden et al. (2000) J Biotechnol 81, 167-78; Pietras et al. (2001) Cancer Res 61, 2929-34; Jellinek et al. (1995) Biochemistry 34, 11363-72; and Jellinek et al. (1994) Biochemistry 33, 10450-6). Aptamers against VEGF shrink tumors in mice and have shown promise for the treatment of macular dysfunction (see, e.g. Martin et al. (2002) Retina 22, 143-52; and Kim et al. (2002) Proc Natl Acad Sci USA 99, 11399-404). An aptamer against the proinflammatory cytokine oncostatin M is being evaluated for use against rheumatoid arthritis (see, e.g. Rhodes et al. (2000) J Biol Chem 275, 28555-61), and aptamers against blood coagulation factors VIIa and IXa are under investigation as anticoagulants (see, e.g. Rusconi et al. (2000) Thromb Haemost 84, 841-8; and Rusconi et al. (2002) Nature 419, 90-4).

As a target for aptamer selection, RTKs stand out through their large size. The extracellular domains of type I RTKs are heavily glycosylated, may form several higher molecular weight complexes, and a variety of distinct conformations are likely to exist. These differences pose a considerable challenge for the application of SELEX to RTKs. HER3 exemplifies these challenges, because of its high propensity to self-associate. Consequently, there is a need in the art for methods that allow the identification aptamers to RTKs such as HER3 as well as specific aptamers that recognize these molecules. The invention disclosed herein satisfies this need.

SUMMARY OF THE INVENTION

In the invention disclosed herein, SELEX methodology was utilized to select RNA aptamers against the oligomeric states of the extracellular domains of HER3 (HER3ECD, monomeric m.w. 82,000 D). A number of specific RNA aptamers against the oligomeric states of the extracellular domains of HER3 and methods for making and using these aptamers are disclosed herein. One of the aptamers, A30, binds with high affinity to a limited number of binding sites in the oligomeric state of HER3ECD. Binding of A30 and the HER3 ligand heregulin are not competitive. Instead, the disruption of HER3 oligomers by heregulin results in an almost tenfold increase in total binding sites, but the newly created binding sites are of lower affinity. High affinity binding of A30 inhibits heregulin-dependent tyrosine phosphorylation of HER2 as well as the heregulin induced growth response of MCF7 cells. As an example of an aptamer against a large macromolecular protein complex, A30 can serve as a tool for the analysis of receptor interactions and may serve as a lead compound for the development of inhibitors against overexpressed RTKs in pathologies associated with HER3 overexpression such as cancer.

The invention disclosed herein has a number of embodiments. One embodiment of the invention is an isolated nucleic acid molecule that binds HER3 polypeptide (SEQ ID NO: 2), wherein the nucleic acid molecule comprises the sequence: 5'-CAGCGAAAGUUGCGUAUGGGUCA-CAUCGCAG-3' (SEQ ID NO: 19). In specific illustrative embodiments of the invention, the nucleic acid molecule comprises the sequence shown in SEQ ID NO: 7, SEQ ID NO: 12, SEQ ID NO: 15, SEQ ID NO: 16, SEQ ID NO: 17 or SEQ ID NO: 18. In addition, the nucleic acid molecules of the invention typically form a triple hairpin loop structure as shown in FIG. 10 and further comprises a stem structure as shown in FIG. 10, wherein the stem structure has at least 1, 2, 3, 4, 5 or 6 base pairings.

Optionally, a nucleic acid molecule of the invention is contained within a pharmaceutical composition, for example a pharmaceutical carrier, excipient or stabilizer. In certain embodiments of the invention, the nucleic acid molecule can be labeled with a detectable marker. Other embodiments of the invention include a vector comprising the nucleic acid molecules of the invention, for example DNA vectors (wherein thymidine (T) replaces uridine (U)) and/or host cells comprising such vectors.

Embodiments of the invention include a variety of methods for using the disclosed nucleic acid molecules for example as probes for HER3 polypeptides. One typical embodiment is a method of binding a nucleic acid molecule comprising the sequence 5'-CAGCGAAAGUUGCGUAUGGGUCA-CAUCGCAG-3' (SEQ ID NO: 19) to a HER3 polypeptide encoded by a polynucleotide of SEQ ID NO: 1 comprising combining the nucleic acid molecule and the HER3 polypeptide for a time and under conditions effective to allow the nucleic acid molecule to bind to the HER3 polypeptide such that said binding occurs. In certain embodiments of such methods, the nucleic acid molecule and the HER3 polypeptide are combined in vitro (e.g. in a patient biopsy sample). Alternatively, the nucleic acid molecule and the HER3 polypeptide are combined in vivo (e.g. in a therapeutic regimen that treats a patient suffering from a pathology characterized by a disregulation of a biological pathway associated with HER3, HER2 and/or heregulin). Embodiments of the invention can include additional methodological steps such as examining the HER3 polypeptide for evidence of said binding via protocols such as a native gel mobility shift assay. Optionally, the nucleic acid molecule is labeled with a detectable marker.

In certain embodiments of the invention, the methods include examining the affinity of the nucleic acid molecule for the HER3 polypeptide and/or the number of binding sites for the nucleic acid molecule present on the HER3 polypeptide. In an illustrative embodiment of the invention, the nucleic acid molecule is combined with HER3 polypeptide expressed on the surface of a human cell and the method further comprises the step of examining the affinity of the nucleic acid molecule for the HER3 polypeptide. In yet another embodiment of the invention, the nucleic acid molecule is combined with HER3 polypeptide expressed on the surface of a human cell and the method further comprises the step of examining the number of nucleic acid molecule binding sites in the HER3 polypeptide.

Alternative embodiments of the invention can include additional methodological steps such as examining the HER3 polypeptide for evidence of said binding via protocols which examine the HER3 polypeptide and/or the modulation of one or more activities of the biological pathway associated with HER3, HER2 and/or heregulin. In one embodiment, the nucleic acid molecule is combined with HER3 polypeptide expressed on the surface of a human cell that further expresses HER2 polypeptide (SEQ ID NO: 6) and the method further comprises examining the human cell for evidence of said binding, wherein the inhibition of heregulin (SEQ ID NO: 4) induced tyrosine phosphorylation of HER2 in the human cell provides evidence of said binding. In another embodiment, the nucleic acid molecule is combined with HER3 polypeptide expressed on the surface of a human cell that further expresses HER2 polypeptide (SEQ ID NO: 6) and the method further comprises examining the human cell for evidence of said binding, wherein the inhibition of heregulin (SEQ ID NO: 4) induced growth in the human cell provides evidence of said binding.

Another typical embodiment of the invention is a method of modulating heregulin mediated signalling in a mammalian cell, wherein the cell expresses a HER2/HER3 complex on the surface of the cell, the method comprising contacting the cell with an aptamer polynucleotide disclosed herein under conditions that allow the aptamer polynucleotide to interact with an extracellular portion of a HER3 polypeptide expressed by the cell so that heregulin mediated signaling in the mammalian cell is modulated. In a specific embodiment of the invention, the modulation of heregulin mediated signalling in a mammalian cell comprises an inhibition of heregulin mediated signalling (e.g. using the A30 aptamer). In an alternative embodiment, the modulation of heregulin mediated signalling in a mammalian cell comprises an enhancement of heregulin mediated signalling (e.g. using the A18 aptamer). In preferred embodiments, the modulation of heregulin mediated signalling in a mammalian cell comprises an inhibition of heregulin mediated signalling the mammalian cell is a human breast cancer or ovarian cancer cell.

The invention disclosed herein further provides articles of manufacture and kits which include reagents for performing for example, the methods disclosed herein. One illustrative embodiment is a kit comprising a nucleic acid molecule comprising the sequence 5'-CAGCGAAAG-UUGCGUAUGGGUCACAUCGCAG-3' (SEQ ID NO: 19) and methods for its use.

BRIEF DESCRIPTION OF THE FIGURES

FIG. 1: Design of aptamers and sequences of six selected aptamers with affinity for HER3ECD. The initial aptamer library was created by PCR of the indicated DNA template, containing a randomized core of 49 nucleotides (SEQ ID NO: 14). The primers for the PCR are indicated underneath the template. The aligned sequences represent the randomized core of six of the 29 clones that were selected based on robust binding in gel shift assays with HER3ECD. For example, the 49 nucleotide A6 aptamer core sequence within the indicated DNA template has the sequence 5'-TAATACGACTCACTAT-AGGGAATTCCGCGTGTGCAGAACAATCGCATAGGC CGCAAGGTTAGTTTCGTTGTCCGCCCG-GTGCAGTCCGTTCGGGATCCTC-3' (SEQ ID NO: 20, as this is described as a DNA template, "U" is therefore replaced with "T"). A6, A18, A19, A23, A30 and A37 in this figure correspond to SEQ ID NOS: 8-13 respectively. The same six aptamers were used for the inhibition studies, shown in FIG. 2.

FIG. 9: A comparison of various A30 embodiments of the invention (from top to bottom: SEQ ID NOS: 15, 16, 17, 12 and 7) as well as an A30 consensus sequence (SEQ ID NO: 18) and the A30 minimal loop sequence (SEQ ID NO: 19).

DETAILED DESCRIPTION OF THE INVENTION

Figure 2:
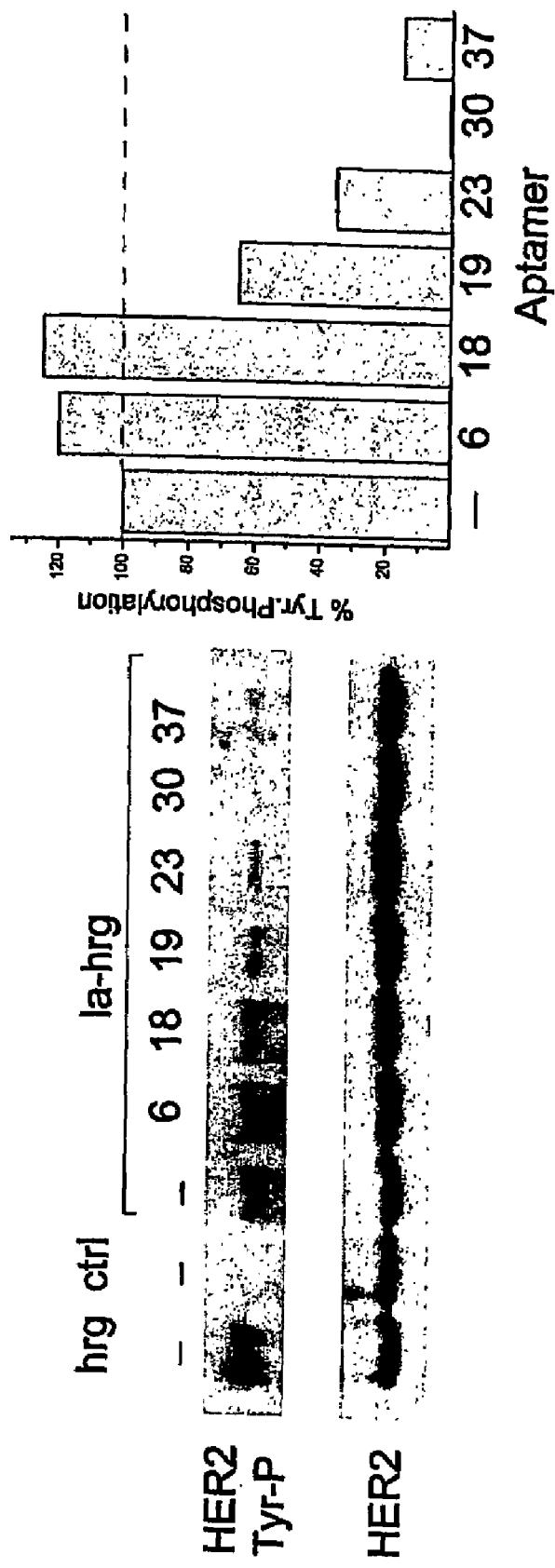
FIG. 2: Screening of selected aptamers for their inhibition of biological activities associated with HER2 activation by heregulin. MCF7 cells were either stimulated with 10 nM wild type heregulin (hrg) or low affinity heregulin (la-hrg) in the presence of 100 nM of the various aptamers indicated. Tyrosine phosphorylation of HER2 was determined by Western blotting. The numbers above each lane indicate aptamer clones. While A30 reduces tyrosine phosphorylation almost to the level observed for the unstimulated control (Ctrl), other aptamers, such as A6 and A18, enhance the activation by low affinity heregulin. The level of tyrosine phosphorylation in the presence of the various aptamers is shown in column format to the right, relative to the uninhibited stimulation with la-hrg (−). The differences in tyrosine phosphorylation of HER2 are not due to changes in the levels of HER2, visualizes by direct detection of the receptor.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook and Russel, 2001, Molecular Cloning: A Laboratory Manual, 3d ed., Cold Spring Harbor Laboratory Press, Cold Spring Harbor, N.Y. and Ausubel et al., Current Protocols in Molecular Biology, Wiley Interscience Publishers, (1995). As appropriate, procedures involving the use of commercially available kits and reagents are generally carried out in accordance with manufacturer defined protocols and/or parameters unless otherwise noted.

I. Definitions

As used herein, the term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T) can also be uracil (U); this definition pertains to the differences between the chemical structures of DNA and RNA, in particular the observation that one of the four major bases in RNA is uracil (U) instead of thymidine (T).

As used herein, the term "polypeptide" means a polymer of at least about 4, 5, 6, 7, or 8 amino acids. Throughout the specification, standard three letter or single letter designations for amino acids are used. In the art, this term is often used interchangeably with "peptide" or "protein".

"Isolated," when used to describe the various molecules disclosed herein, means for example a polynucleotide molecule that has been identified and separated and/or recovered from a component of the environment in which the molecule is produced. Contaminant components of this environment are materials that would typically interfere with diagnostic or therapeutic uses for the polynucleotides of the invention, and may include polypeptides and polynucleotides, and other proteinaceous or non-proteinaceous solutes.

"Growth inhibition" when used herein refers to the growth inhibition of a cell in vitro and/or in vivo. The inhibition of cell growth can be measured by a wide variety of methods known in the art including those described in the Examples below. A "growth inhibitory agent" when used herein refers to a compound or composition which inhibits growth of a cell in vitro and/or in vivo. Thus, a growth inhibitory agent may be one which significantly reduces the percentage of cells in S phase. Examples of growth inhibitory agents include agents that block cell cycle progression (at a place other than S phase), such as agents that induce G1 arrest and M-phase arrest Classical M-phase blockers include the vincas (vincristine and vinblastine), TAXOL®), and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (W B Saunders: Philadelphia, 1995), especially p. 13.

"Biologically active" or "biological activity" for the purposes herein means (a) having the ability to modulate the activity and/or function of a polypeptide such as heregulin, HER2 and/or HER3; and/or (b) having the ability to modulate the growth of at least one type of mammalian cancer cell or experimentally transformed cell in vivo or ex vivo.

The terms "agonist" and "agonistic" when used herein refer to a molecule which is capable of, directly or indirectly, substantially inducing, promoting or enhancing biological activity or activation of a molecule such as heregulin, HER2 or HER3. The term "antagonist" when used herein refers to a molecule which is capable of, directly or indirectly, substantially inhibiting the biological activity or activation of a molecule such as heregulin, HER2 or HER3.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of conditions like cancer. Examples of chemotherapeutic agents include alkylating agents alkyl sulfonates such as busulfan; aziridines such as benzodopa, antimetabolites such as methotrexate; folic acid analogues such as denopterin; taxoids, e.g. paclitaxel (TAXOL®, Bristol-Myers Squibb Oncology, Princeton, N.J.) and doxetaxel (TAXOTERE®, Rhône-Poulenc Rorer, Antony, France); platinum analogs such as cisplatin; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Eareston); and anti-androgens such as flutamide, nilutamide, bicalutamide, leuprolide, and goserelin; and pharmaceutically acceptable salts, acids or derivatives of any of the above.

The term "cytokine" is a generic term for proteins released by one cell population which act on another cell as intercellular mediators. Examples of such cytokines are lymphokines, monokines, and traditional polypeptide hormones. Included among the cytokines are heregulin, growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integtin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

"Treatment" or "therapy" refer to both therapeutic treatment and prophylactic or preventative measures.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing tumor burden or volume, the time to disease progression (TTP) and/or determining the response rates (RR).

"Mammal" for purposes of treatment or therapy refers to any animal classified as a mammal including humans, domestic and farm animals, and zoo, sports, or pet animals, such as dogs, horses, cats, cows, etc. Preferably, the mammal is human.

The terms "cancer", "cancerous", or "malignant" refer to or describe the physiological condition in mammals that is typically characterized by unregulated cell growth. Examples of cancer include but are not limited to, carcinoma, lymphoma, blastoma, sarcoma, and leukemia. More particular examples of such cancers include breast cancer, ovarian cancer, colon cancer, colorectal cancer, rectal cancer, squamous cell cancer, small-cell lung cancer, non-small cell lung cancer, Hodgkin's and non-Hodgkin's lymphoma, testicular cancer, esophageal cancer, gastrointestinal cancer, renal cancer, pancreatic cancer, glioblastoma, cervical cancer, glioma, liver cancer, bladder cancer, hepatoma, endometrial carcinoma, salivary gland carcinoma, kidney cancer, liver cancer, prostate cancer, vulval cancer, thyroid cancer, hepatic carcinoma and various types of head and neck cancer. Diagnosis in mammals of the various pathological conditions described herein can be made by the skilled practitioner. Diagnostic techniques are available in the art which allow, e.g., for the diagnosis or detection of cancer or immune related disease in a mammal. For instance, cancers may be identified through techniques, including but not limited to, palpation, blood analysis, x-ray, NMR and the like.

II. Characterization of Aspects of the Invention

The disclosure provided herein reports the successful selection of aptamers specific for the extracellular domains of HER3. SELEX requires a high abundance of target and selection against proteins the size of HER3ECD creates special challenges. At elevated concentrations HER3ECD exists in an oligometic form. This represents, to our knowledge, the largest target for successful aptamer selection to date. Some observed differences to "more conventional" SELEX may therefore be a reflection of the large size of the target surface. Most notably, our selection resulted in a family of aptamers without apparent consensus. At least two classes of aptamers were apparent, causing either inhibition or enhancement of heregulin dependent activation. Those two classes are represented by A30 and A18 respectively, which showed no mutual competition for binding in gel-shift studies. These findings provide evidence that the lack of sequence convergence is at least in part a reflection of selection against different binding sites.

Figure 3:
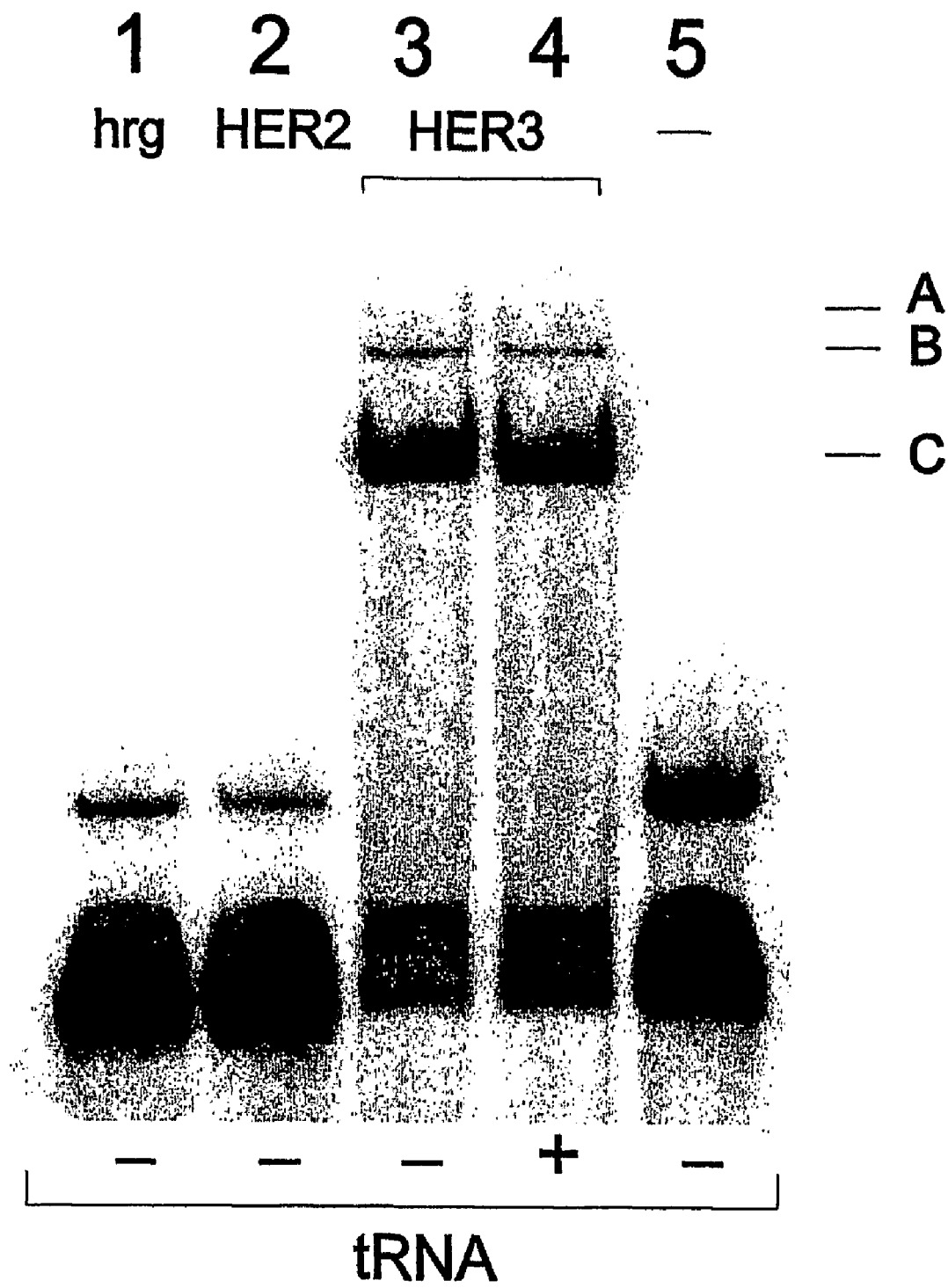
FIG. 3: Native gel mobility shift assay of radiolabeled A30. Radiolabeled A30 (alone=Ctrl) is shifted to several slower migrating species in the presence of purified HER3ECD (0.5 µM). This interaction does not occur with HER2-ECD or heregulin, both 0.5 µM, and is not inhibited by an excess of tRNA (4 µM).

The selected aptamers show high specificity for HER3ECD. We analyzed A30 in more detail. Despite a high level of homology between the ECDs of HER2 and HER3, A30 shows no binding to the ECD of HER2 or to heregulin, even at concentrations far above those used in inhibition studies (FIG. 3). Most aptamers obtained during the selection show no binding to HER3ECD, providing a randomized control set for unspecific binding. Non-specific RNA FIG. 3) as well as aptamer with independent binding to HER3ECD (A18) do not interfere with the binding of A30 to HER3ECD.

On a cellular level, we cannot exclude the possibility of additional low affinity targets. However, the inhibitory properties of A30 are directly linked to the action of heregulin. A30 does not exhibit general growth inhibition but specifically inhibits the growth stimulatory component elicited by heregulin. While heregulin-induced tyrosine phosphorylation of HER2, which proceeds primarily through HER2-HER3 complexes, is inhibited, the activation of HER2 by EGF, requiring dimers of EGFR-HER2, is not inhibited.

The inhibitory properties of A30 raise the question about possible modes of binding and the method by which signaling is inhibited. At present, we have no information on the localization of the A30 binding site on the HER3ECD. However, the fact that A30 binding is not competitive with heregulin and the size of the aptamer make it less likely that domains 1-3 of the ECD, involved in ligand binding, are the target. Recent models of HER3 activation, based on the crystal structure of the HER3ECD and ECD of EGFR with bound ligand (see, e.g. Cho et al. (2002) Science 297, 1330-3; and Ogiso et al. (2002) Cell 110, 775-87), assume receptor interactions in domains 2 and 4 in the activated complex of HER2 and HER3 (see, e.g. Schlessinger, J. (2003) Science 300, 750-2). At present, domain 4 appears to be the most likely target for A30 and aptamer binding is therefore anticipated to interfere with the dimerization of HER2 and HER3 but not heregulin binding. In the crystal structure, domains 2 and 4 of HER3ECD are also involved in an intramolecular "lock".

Figure 5:
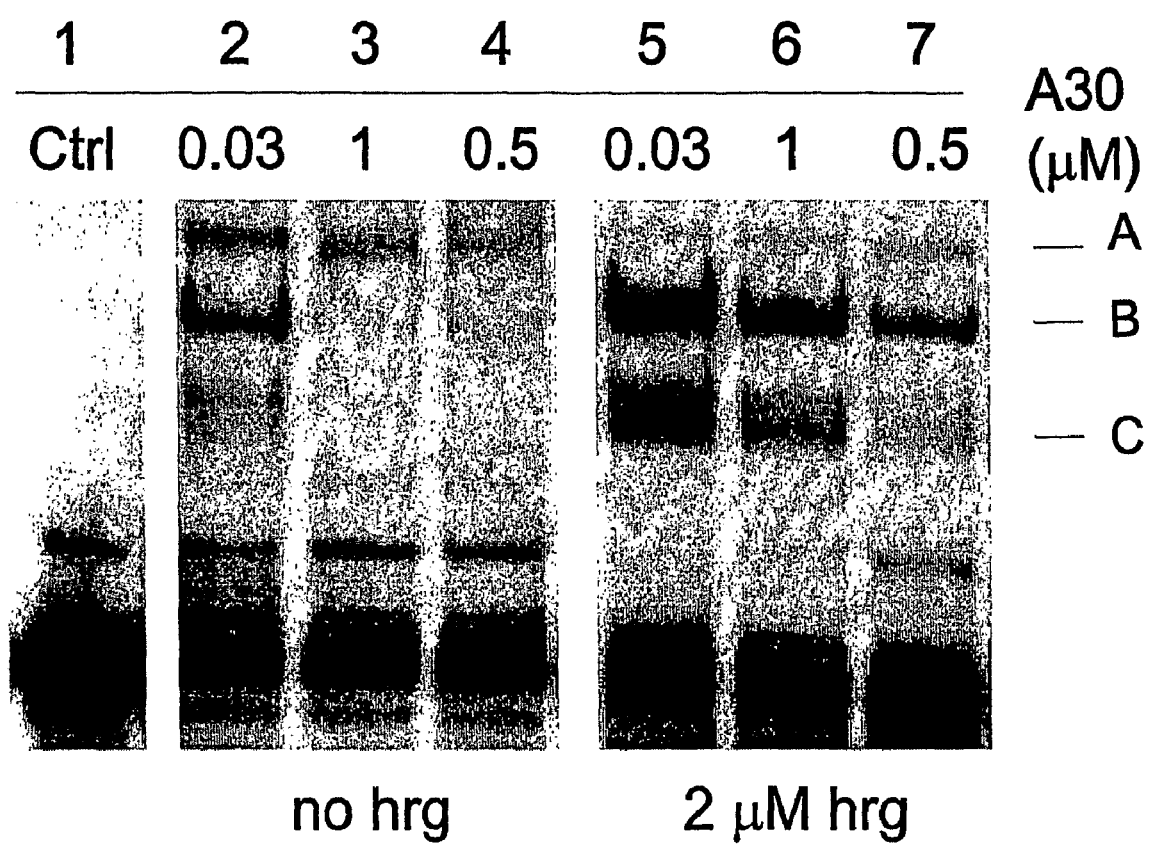
FIG. 5: Gelshift pattern of A30 and HER3ECD in the presence and absence of heregulin and competition with unlabeled A30. The binding of radiolabeled A30 to HER3ECD (0.5 µM) is shown at various concentration of total A30 (shown in µM). Addition of a molar excess of heregulin (lanes 5-7) enhances binding, but does not qualitatively change the pattern of shifted bands (A, B, C).
Figure 6:
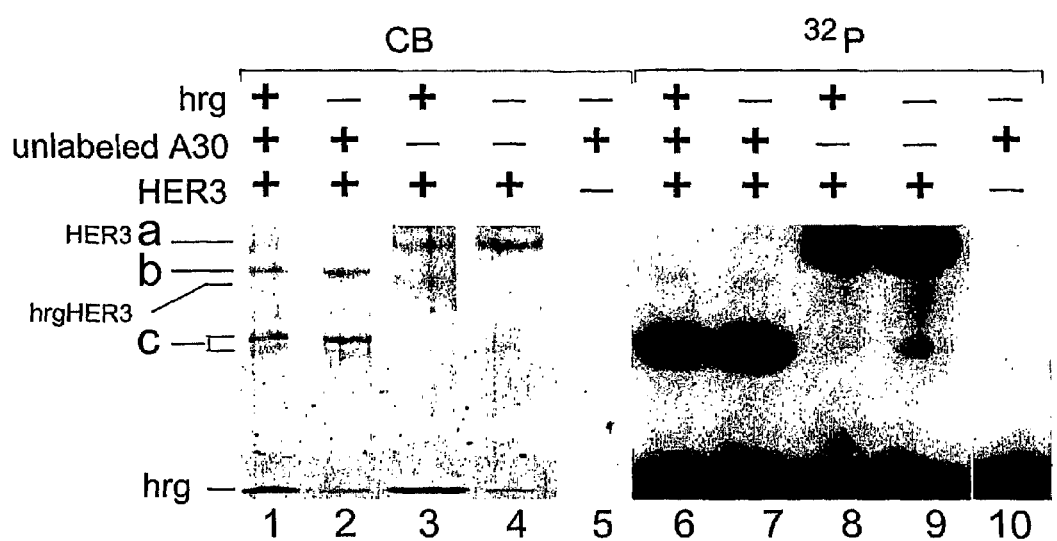
FIG. 6: Gelshift of radiolabeled A30 and direct visualization of HER3ECD at elevated protein concentrations. Radiolabeled A30 (0.3 nM) is present in all lanes. The concentration of HER3ECD is 2 µM and heregulin (6 µM) and unlabeled A30 (8 µM) were added at a molar excess as indicated above the gel. Gels were either analyzed by direct coomassie staining (CB) or autoradiography ($^{32}$P) as indicated. On this 4-15% Phast gel, both heregulin and A30 run with the running front.

The analysis of the mode of binding of A30 to HER3ECD shows the presence of at least two different modes of interaction, evident by the presence of multiple gelshifted species (FIGS. 3, 5 and 6). Without being bound by a specific scientific theory, the current working model for the effect of heregulin on A30 binding assumes that A30 preferentially binds oligomers of HER3ECD. Given that aptamers were initially selected at high concentrations of HER3ECD, oligomers of HER3 would have been the primary target of selection. This hypothesis is also consistent with several experimental findings. At high concentrations of HER3ECD (FIG. 6), disruption of oligomers by excess heregulin is incomplete. Under those conditions of partial disruption of oligomers and an excess of oligomers over A30 FIG. 6, lane 8), oligomers of HER3ECD are the preferred binding site for A30. However, the number of accessible sites in the oligomeric species appears to be limited. Based on this model, the heregulin-induced increase in A30 binding sites at lower concentrations of HER3ECD would reflect the more complete disruption of oligomers by heregulin, resulting in increased access for A30 to the ECD but the resulting binding sites have reduced affinity. One possible explanation for the different interaction with oligomers and monomers assumes a binding surface on the oligomers that contains residues from adjacent ECD molecules at the periphery of ECD clusters. A disruption of oligomers would make individual ECDs more accessible but part of the binding interface would be lost, resulting in weaker binding. Further, support for the notion of substoichiometric binding of A30 to HER3 oligomers comes also from the fact that the maximum number of cellular binding sites for A30 (3250±200) falls short of the total number of HER3 receptors (25,000) in MCF7 cells. This discrepancy is partially reduced by the addition of heregulin. This partial disruption of HER3 oligomers on the cell surface is consistent with the partial disruption of high concentrations of soluble ECDs in solution, even in the presence of excess heregulin.

If A30 is in fact capable of binding to HER3ECD monomers, albeit with lower affinity, a large excess of A30 should disrupt oligomers of HER3ECD. Evidence for such a disruption is provided in FIG. 6 (lane 2 versus 4). In our model, based on a transition of HER3ECD oligomers to monomers, (species a, lane 8 and 9 of FIG. 6) would represent the binding of a single A30 to the oligomer under conditions of a large excess of oligomeric HER3ECD. High concentrations and a molar excess of A30 over HER3ECD would stabilize the monomeric form of HER3ECD and would also result in complete saturation of all accessible binding sites on the remaining oligomer. The high negative net charge of such a complex should result in a significantly shifted oligomeric species.

Assuming that species b represents such a shifted oligomer while species c represent a monomer complex, the low ratio of A30 per HER3ECD (FIG. 6, lane 2) is consistent with a substoichiometric number of accessible sites on the oligomer.

While not being bound by a specific scientific theory, the above model provides a simple working hypothesis for the mechanism of A30 binding to HER3ECD. The model does not account for the double band for species c (FIG. 6, lane 1 and 2) and species C in FIG. 5. The crystal structure of HER3ECD suggests two distinct conformations of HER3ECD (open and locked). Such differences in conformation could contribute to differences in migration of A30-monomer complexes. Also, alternative explanations, such as species with a different stoichiometry of A30 binding to HER3ECD monomers, cannot be ruled out at this point.

Figure 7:
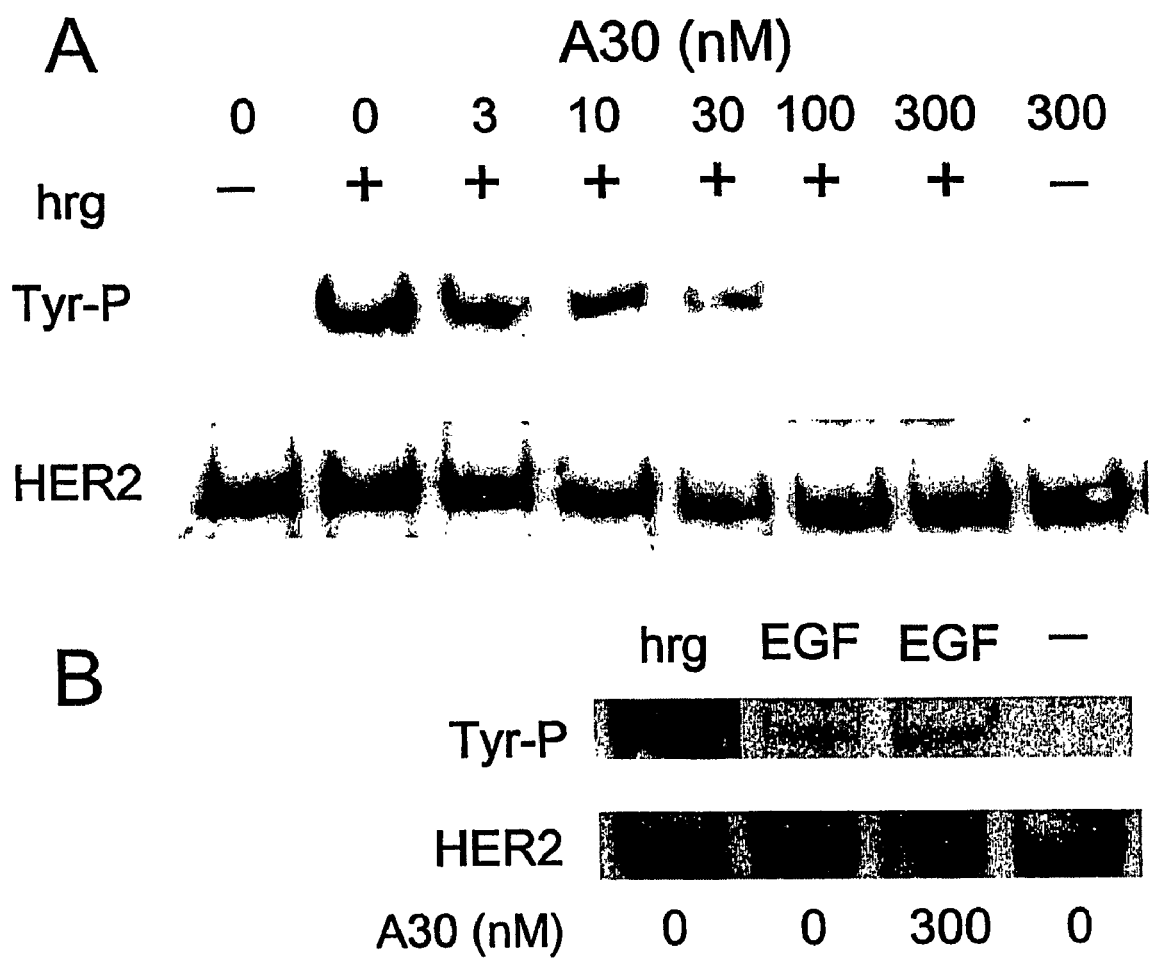
FIG. 7: Inhibition of HER2/HER3 activation by A30. A) Anti-phosphotyrosine Western blot of MCF7 cell lysates after HER2 immunoprecipitation. Cells were stimulated with wild type heregulin (5 nM) unless indicated otherwise (−). A30 was added at the concentrations indicated above each lane. The differences in tyrosine phosphorylation of HER2 are not due to changes in the levels of HER2, visualizes by direct detection of the receptor. B) Tyrosine phosphorylation of HER2 following stimulation with EGF is not inhibited by A30. EGF or heregulin were added to MCF7 cells at 5 nM in the presence or absence of A30 (300 nM).

Regardless of the complexities of the mechanism of binding by A30, the data demonstrate that the selected aptamer is specific for HER3ECD and inhibits the hetegulin-induced activation of HER3/HER2 (FIG. 7). The lack of competition between heregulin and A30 indicates that the inhibitory effect of A30 on tyrosine phosphorylation is not due to inhibition of heregulin binding. The activity of A30 and similar aptamers against HER3 may complement antibodies that target HER2, especially in cases where elevated levels of HER3 enhance the effect of HER2 overexpression.

We have generated an aptamer against the extracellular domains of HER3. The ease with which aptamers can be chemically modified makes them ideal starting points for the synthesis of a broad range of biochemical tools that may shed light into the complex interactions between receptor tyrosine kinases in a membrane setting. Given that A30 has not been subjected to further modifications that could enhance its serum stability and binding affinity, it already shows a remarkably strong inhibitory effect on heregulin-induced growth stimulation of MCF7 cells. The mechanism of inhibition by A30 is likely to be complex and requires further analysis. Additional contributions beyond the direct targeting of HER3 cannot be ruled out at this point. However, the inhibitory properties of A30 demonstrate its potential usefulness as a lead compound for the design of anticancer drugs. The activity of A30 is of special importance in light of the paradigm established by Herceptin. Herceptin has demonstrated that a non-toxic and non-membrane permeating macromolecule has the potential to be a potent reagent in the treatment of cancer. Anti-HER3ECD aptamers, in isolation or in combination with other treatments such as anti-HER2 antibodies or anti-HER3 aptamers that bind different binding sites, may therefore become a valuable addition to the repertoire of inhibitors that target cancers that overexpress HER2.

The invention provides methods for modulating HER3, and/or heregulin activity in mammalian cells which comprise exposing the cells to a desired amount of HER3 aptamer that affects heregulin mediated HER3 activation. Preferably, the amount of HER3 aptamer employed will be an amount effective to affect the binding and/or activity of the respective ligand or respective receptor to achieve a therapeutic effect. This can be accomplished in vivo or ex vivo in accordance, for instance, with the methods described below. Exemplary conditions or disorders to be treated with HER3 aptamers include cancer such as those associated with an aberrant expression of HER2, HER3 and/or heregulin. In particular, the molecules described herein are useful in treating various pathological conditions associated with the disregulation of the biological activities associated with heregulin, HER2 and/or HER3, such as cancer (see, e.g. Stove et al., J Invest Dermatol. 2003 October;121(4):802-12; Earp et al., Trans Am Clin Climatol Assoc. 2003;114:315-33; Mendoza et al., Cancer Res. 2002 Oct. 1;62(19):5485-8; Kumar et al., Semin Oncol. 2001 October;28(5 Suppl 16):27-32; S chelfhout et al., J Natl Cancer Inst. 2000 Apr. 19;92(8):622-8; Gilbertson et al., Cancer Res. 1997 Aug. 1;57(15):3272-80; Gullick Cancer Surv. 1996;27: 339-49; and Wallasch et al., EMBO J. 1995 Sep. 1;14(17): 4267-75). These conditions can be treated by modulating a selected activity associated with heregulin mediated activation of the HER3 associated receptor complex in a mammal through, for example, administration of one or more HER3 aptamers described herein.

The HER3 aptamers can be administered in accord with known methods, such as intravenous administration as a bolus or by continuous infusion over a period of time, by intramuscular, intraperitoneal intracerebrospinal, subcutaneous, intra-articular, intrasynovial, intrathecal oral, topical, or inhalation routes. Optionally, administration may be performed through mini-pump infusion using various commercially available devices. Effective dosages and schedules for administering antagonists or agonists may be determined empirically, and making such determinations is within the skill in the art. Single or multiple dosages may be employed. Interspecies scaling of dosages can be performed in a manner known in the art, e.g., as disclosed in Mordenti et al., *Pharmaceut. Res.*, 8:1351 (1991).

As noted above, the HER3 aptamers useful in the methods of the invention can be incorporated into pharmaceutical compositions suitable for administration into a mammal. Such compositions typically comprise at least one HER3 aptamer and a pharmaceutically acceptable carrier. Methods for formulating the HER3 aptamer compounds of the invention for pharmaceutical administration are known to those of skill in the art. See, for example, Remington: The Science and Practice of Pharmacy, 19$^{th}$ Edition, Gennaro (ed.) 1995, Mack Publishing Company, Easton, Pa.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the, invention is formulated to be compatible with its intended route of administration.

The pharmaceutical compositions of the invention, comprising HER3 aptamers, are administered in therapeutically effective amounts. The "therapeutically effective amount" refers to a nontoxic dosage level sufficient to induce a desired biological result (e.g. a diminution of the severity of the symptoms associated with a pathological condition such as breast or ovarian cancer). Amounts for administration may vary based upon the desired activity, the diseased state of the mammal being treated, the dosage form, method of administration, patient factors such as age, sex, and severity of disease. It is recognized that a therapeutically effective amount is provided in a broad range of concentrations. Such range can be determined based on in vitro and/or in vivo assays.

Therapeutic compositions of the HER3 aptamers can be prepared by mixing the desired molecule having the appropriate degree of purity with optional pharmaceutically acceptable carriers, excipients, or stabilizers (*Remington's Pharmaceutical Sciences,* 16th edition, Osol, A. ed. (1980)), in the form of lyophilized formulations, aqueous solutions or aqueous suspensions. Acceptable carriers, excipients, or stabilizers are preferably nontoxic to recipients at the dosages and concentrations employed, and include buffers such as Tris, HEPES, PIPES, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; sugars such as sucrose, mannitol, trehalose or sorbitol; salt-forming counter-ions such as sodium; and/or non-ionic surfactants such as TWEEN™, PLURONICS™ or polyethylene glycol (PEG).

Additional examples of such carriers include ion exchangers, alumina, aluminum stearate, lecithin, serum proteins, such as human serum albumin, buffer substances such as glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, colloidal silica, magnesium trisilicate, polyvinyl pyrrolidone, and cellulose-based substances. Carriers for topical or gel-based forms include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations.

Solutions or suspensions used for administering HER3 aptamers can include the following components: a sterile diluent such as water for injection, saline solution; fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates and agents for the adjustment of tonicity such as sodium chloride or dextrose. In one embodiment, a pharmaceutical composition can be delivered via slow release formulation or matrix comprising HER3 aptamers or DNA constructs suitable for expression of HER3 aptamer in or around a site within the body.

HER3 aptamers can also be administered in the form of a variety of sustained-release preparations. For example, HER3 aptamers may be delivered to the lung for slow release via encapsulation or carrier materials such as liposomes, or other drug "shells" such as albumin (Albunex by Molecular Biosystems), sugars (Levovist by Schering), gelatins, or lipids. Other suitable examples of sustained-release preparations for use with polypeptides including semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.*, 15: 167-277 (1981) and Langer, *Chem. Tech.*, 12: 98-105 (1982) or poly(vinylalcohol)), polylactides (U.S. Pat. No. 3,773,919, EP 58,481), copolymers of L-glutamic acid and gamma ethyl-L-glutamate (Sidman et al., *Biopolymers*, 22: 547-556 (1983)), non-degradable ethylene-vinyl acetate (Langer et al., supra), degradable lactic acid-glycolic acid copolymers such as the Lupron Depot (injectable microspheres composed of lactic acid-glycolic acid copolymer and leuprolide acetate), and poly-D-(−)-3-hydroxybutyric acid (EP 133,988).

The route of administration may vary depending on the desired effect and/or outcome. Generally for modulation of an HER3 mediated response, introduction of the HER3 aptamer at or near the desired site of response is utilized. Alternatively additional routes of administration, such as a systemic administration of HER3 aptamers, may be employed. Examples of routes of administration include parenteral, e.g., intravenous, intradermal, intramuscular, subcutaneous, et al. (e.g., inhalation) transdermal (topical), transmucosal (e.g. a nasal spray), and rectal administration. The HER3 aptamer may also be administered by perfusion techniques, such as isolated tissue perfusion, to exert local therapeutic effects. Solutions or suspensions used for parenteral, intradermal, or subcutaneous application can include the following components: a sterile diluent such as water for injection, saline solution; fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates and agents for the adjustment of tonicity such as sodium chloride or dextrose. Regimens of administration may vary. A single dose or multiple doses of the agent may be used. Such regimens can vary depending on the severity of the disease and the desired outcome. Following administration of a HER3 aptamer to the mammal, the mammal's physiological condition can be monitored in various ways well known to the skilled practitioner familiar with the pathological condition to be treated (e.g. breast or ovarian cancer).

It is contemplated that yet additional therapies may be employed in the methods. The one or more other therapies may include but are not limited to, administration of radiation therapy, cytokine(s), growth inhibitory agent(s), chemotherapeutic agent(s), cytotoxic agent(s), tyrosine kinase inhibitors, ras farnesyl transferase inhibitors, angiogenesis inhibitors, and cyclin-dependent kinase inhibitors which are known in the art. In addition, therapies based on therapeutic antibodies that target tumor antigens such as Rituxan™ or Herceptin™ as well as anti-angiogenic antibodies such as anti-VEGF.

Preparation and dosing schedules for chemotherapeutic agents may be used according to manufacturers' instructions or as determined empirically by the skilled practitioner. Preparation and dosing schedules for such chemotherapy are also described in *Chemotherapy Service* Ed., M. C. Petry, Williams & Wilkins, Baltimore, Md. (1992). The chemotherapeutic agent may precede, or follow administration of, e.g. an aptamer, or may be given simultaneously therewith. The aptamer, for instance, may also be combined with an anti-oestrogen compound such as tamoxifen or an anti-progesterone such as onapristone (see, EP 616812) in dosages known for such molecules.

III. TYPICAL EMBODIMENTS OF THE INVENTION

Figure 10A:
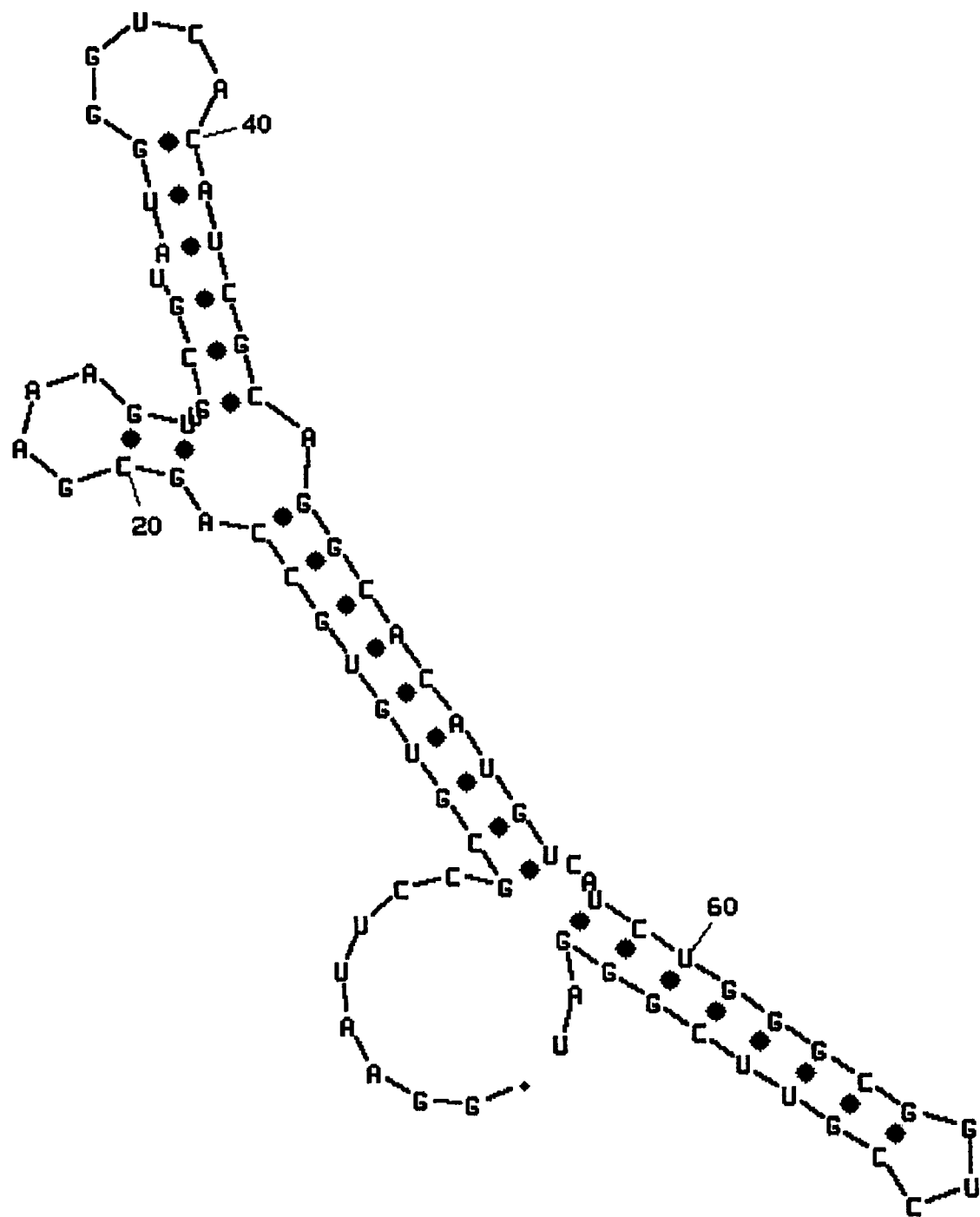
FIGS. 10A and 10B: Hairpin loop and stem structures formed by A30 embodiments of SEQ ID NO: 16 and SEQ ID NO: 7 respectively. Both A30 embodiments of SEQ ID NO: 7 and SEQ ID NO: 16 exhibit a triple hairpin loop structure formed by the nucleotides identified in SEQ ID NO: 19. The A30 embodiment shown in SEQ ID NO: 7 comprises a stem structure having 6 base pairings.
Figure 10B:
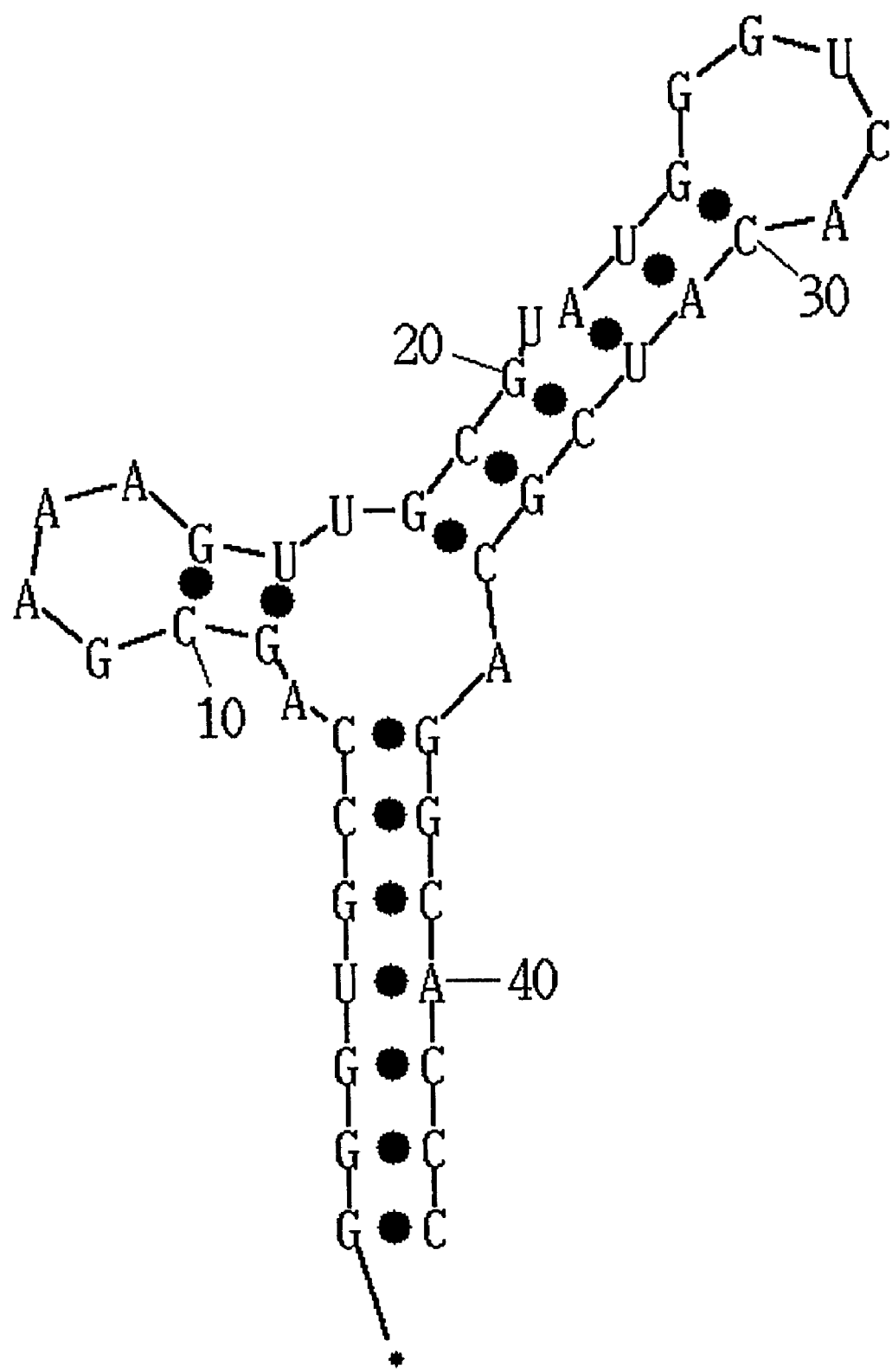

The invention disclosed herein has a number of embodiments. As is shown in FIG. 10, the A30 aptamer has a number of embodiments, all of which comprise a common nucleotide sequence. Without being bound by a specific scientific theory, it is believed that this common sequence allows the formation a conformation that is associated with aptamer binding. In this context, one embodiment of the invention is an isolated nucleic acid molecule that binds HER3 polypeptide (SEQ ID NO: 2), wherein the nucleic acid molecule comprises the common sequence: 5'-CAGCGAAAGUUGCGUAUGGGU-CACAUCGCAG-3' (SEQ ID NO: 19). In specific illustrative embodiments of the invention, the nucleic acid molecule comprises the specific sequence shown in SEQ ID NO: 7, SEQ ID NO: 12, SEQ ID NO: 15, SEQ ID NO: 16, SEQ ID NO: 17 or SEQ ID NO: 18. Typically, a nucleic acid molecule of the invention is at least 50 to 100 nucleotides in length. In addition, the nucleic acid molecules of the invention typically form a triple hairpin loop structure as shown in FIG. 10 and further comprises a stem structure as shown in FIG. 10 and having at least 1, 2, 3, 4, 5 or 6 base pairing (e.g. A:U or G:C).

Optionally, a nucleic acid molecule of the invention is contained within a pharmaceutical composition, for example a pharmaceutical carrier, excipient or stabilizer. In certain embodiments of the invention, the nucleic acid molecule can be labeled with a detectable market. For example, a nucleic acid molecule probe can be labeled with a detectable marker, such as, for example, a radioisotope, fluorescent compound, bioluminescent compound, a chemiluminescent compound, metal chelator or enzyme. Other embodiments of the invention include a vector comprising the nucleic acid molecules of the invention, for example DNA vectors (wherein thymidine (T) replaces uridine (U)) and/or host cells comprising such vectors.

The RNA aptamers disclosed herein provide a tools for use for example in diagnostic assays designed to detect HER3 in a biological sample. As HER 3 polypeptide is known to be overexpressed in a variety of pathological conditions (e.g. colorectal and breast cancers), HER3 protein expression can serve a prognostic factor in the characterization of these syndromes (see, e.g. Kapitanovic et al., J. Cancer Res. Clin. Oncol. 2000, 126(4): 205-211; and Witton et al., J. Pathol. 2003, 200(3): 290-297). Consequently, diagnostic assays which examine HER3 protein expression can be used in clinical contexts pertaining to the diagnostic, prognostic and therapeutic considerations for patients suffering from diseases characterized by an aberrant expression of this molecule.

In addition, RNA aptamers disclosed herein provide a tools for use in diagnostic assays designed to detect an interaction between HER3 and HER2 in a biological sample. As is known in the art, HER2 and HER3 interact to form a complex that triggers a signalling pathway that is known to be disregulated in a number of pathological conditions including a variety of cancers. Consequently, diagnostic assays which allow medical practitioners to examine the status of these crucial elements within this pathway can provide information that these practitioners can use for example to both confirm the diagnosis of a specific type of pathology as well as to determine the prognostic implications of such diagnoses in an individual having a specific type of pathology.

Profiling experiments designed to characteristic patterns of protein association (e.g. HER2/HER3 oligomerization) that are associated with pathological phenotypes can further be used to determine the optimal therapeutic regimen for treating pathologies exhibiting that pattern of protein association. In particular, the HER2 polypeptide and its associated biological pathways are well known targets for a variety of therapeutic agents. As the association of HER2 and HER3 is a crucial event for the activity of a functioning pathway, assays which examine the status of this association allow practitioners to assess the likely biological effect that a specific therapeutic agent or agents which target this pathway will have in a patient suffering from a pathology character- ized by a disregulation of this HER2/HER3 signalling pathway. See, e.g. Mass, Int. J. Radiat. Oncol. Biol. Phys. 2002, 58(3): 932-940; Anido et al., Clin. Cancer Res. 2003, 9(4): 1274-1283; and Azios et al., Oncogene, 2001, 20(37): 5199-5209.

In view of the above, embodiments of the invention include a variety of methods for using the disclosed nucleic acid molecules. One typical embodiment is a method of binding a nucleic acid molecule comprising the sequence 5'-CAGC-GAAAGUUGCGUAUGGGUCACAUCGCAG-3' (SEQ ID NO: 19) to a HER3 polypeptide encoded by a polynucleotide of SEQ ID NO: 1 comprising combining the nucleic acid molecule and the HER3 polypeptide for a time and under conditions effective to allow the nucleic acid molecule to bind to the HER3 polypeptide such that said binding occurs. As explicitly disclosed herein, the HER3 polypeptide encoded by a polynucleotide of SEQ ID NO: 1 can be a full length HER3 polypeptide as occurs for example on the surface of mammalian cells (see, e.g. Example 5 below) or alternatively can be less than full length such as the HER3ECD used to select the aptamers (see, e.g. Example 2 below). In certain embodiments of such methods, the nucleic acid molecule and the HER3 polypeptide are combined in vitro (e.g. in a patient biopsy sample). Alternatively, the nucleic acid molecule and the HER3 polypeptide are combined in vivo (e.g. in a therapeutic regimen that treats a patient suffering from a pathology characterized by a disregulation of a biological pathway associated with HER3, HER2 and/or heregulin). Embodiments of the invention can include additional methodological steps such as examining the HER3 polypeptide for evidence of said binding via protocols such as a native gel mobility shift assay. Optionally, the nucleic acid molecule is labeled with a detectable marker.

In certain embodiments of the invention, the methods include examining the affinity of the nucleic acid molecule for the HER3 polypeptide and/or the number of binding sites for the nucleic acid molecule present on the HER3 polypeptide. In an illustrative embodiment of the invention, the nucleic acid molecule is combined with HER3 polypeptide expressed on the surface of a human cell and the method further comprises the step of examining the affinity of the nucleic acid molecule for the HER3 polypeptide. In yet another embodiment of the invention, the nucleic acid molecule is combined with HER3 polypeptide expressed on the surface of a human cell and the method further comprises the step of examining the number of nucleic acid molecule binding sites in the HER3 polypeptide.

Alternative embodiments of the invention can include additional methodological steps such as examining the HER3 polypeptide for evidence of said binding via protocols which examine the HER3 polypeptide and/or the modulation of one or more activities of the biological pathway associated with HER3, HER2 and/or heregulin. In one embodiment, the nucleic acid molecule is combined with HER3 polypeptide expressed on the surface of a human cell that further expresses HER2 polypeptide (SEQ ID NO: 6) and the method further comprises examining the human cell for evidence of said binding, wherein the inhibition of heregulin (SEQ ID NO: 4) induced tyrosine phosphorylation of HER2 in the human cell provides evidence of said binding. In another embodiment, the nucleic acid molecule is combined with HER3 polypeptide expressed on the surface of a human cell that further expresses HER2 polypeptide (SEQ ID NO: 6) and the method further comprises examining the human cell for evidence of said binding, wherein the inhibition of heregulin (SEQ ID NO: 4) induced growth in the human cell provides evidence of said binding.

Another typical embodiment is a method of modulating heregulin mediated signalling in a mammalian cell, wherein the cell expresses a HER2/HER3 complex on the surface of the cell, the method comprising contacting the cell with an aptamer polynucleotide disclosed herein under conditions that allow the aptamer polynucleotide to interact with an extracellular portion of a HER3 polypeptide expressed by the cell so that heregulin mediated signalling in the mammalian cell is modulated. In a specific embodiment of the invention, the modulation of heregulin mediated signalling in a mammalian cell comprises an inhibition of heregulin mediated signalling. In an alternative embodiment, the modulation of heregulin mediated signaling in a mammalian cell comprises an enhancement of heregulin mediated signalling. In preferred embodiments, the modulation of heregulin mediated signaling in a mammalian cell comprises an inhibition of heregulin mediated signalling the mammalian cell is a human breast cancer or ovarian cancer cell.

Another typical embodiment is a method of modulating heregulin mediated signalling in a mammalian cell, wherein the cell expresses a HER2/HER3 complex on the surface of the cell, the method comprising contacting the cell with an aptamer polynucleotide disclosed herein under conditions that allow the aptamer polynucleotide to interact with an extracellular portion of a HER3 polypeptide expressed by the cell so that heregulin mediated signaling in the mammalian cell is modulated. In a specific embodiment of the invention, the modulation of heregulin mediated signalling in a mammalian cell comprises an inhibition of heregulin mediated signaling. In an alternative embodiment, the modulation of heregulin mediated signalling in a mammalian cell comprises an enhancement of heregulin mediated signaling. In preferred embodiments, the modulation of heregulin mediated signalling in a mammalian cell comprises an inhibition of heregulin mediated signalling the mammalian cell is a human breast cancer or ovarian cancer cell.

Another embodiment of the invention is a method of identifying the presence of a HER3 polypeptide in a biological sample comprising contacting the biological sample with a aptamer disclosed herein under conditions that allow the aptamer polynucleotide to specifically bind to the HER3 polypeptide; and then examining the biological sample for the presence of a aptamer/HER3 polypeptide complex; wherein the presence of the aptamer/HER3 polypeptide complex identifies the presence of a HER3 polypeptide in the biological sample. Optionally the aptamer is labelled with a detectable label. A related embodiment of the invention is a method of identifying the presence or absence of a heregulin-HER3 polypeptide complex in a biological sample comprising contacting the biological sample with a aptamer disclosed herein under conditions that allow the aptamer polynucleotide to specifically bind to the HER3 polypeptide in the biological sample; and then examining either the affinity at which the aptamers bind the HER3 polypeptide in the biological sample; and/or the number of aptamer binding sites on the HER3 polypeptide in the biological sample; wherein the affinity at which the aptamers bind HER3 and/or the number of aptamer binding sites on HER3 is dependent upon the presence of heregulin so that the affinity at which the aptamers bind HER3 and/or the number of aptamer binding sites on HER3 identifies the presence of heregulin-HER3 polypeptide complex in a biological sample.

Another embodiment of the invention is a method of inhibiting the heregulin mediated activation of a HER2/HER3 receptor complex in a human cancer cell comprising contacting the cell with an aptamer polynucleotide comprising the sequence 5'-CAGCGAAAGUUGCGUAUGGGUCA-CAUCGCAG-3' (SEQ ID NO: 19) under conditions that allow the aptamer polynucleotide to interact with an extracellular portion of a HER3 polypeptide expressed by the cell such that heregulin mediated activation of a HER2/HER3 receptor is inhibited. A related embodiment of the invention is a method of inhibiting the growth of mammalian cancer cells that overexpress HER2 comprising exposing the mammalian cancer cells to a therapeutically effective amount of a composition comprising a polynucleotide having the sequence 5'-CAGCGAAAGUUGCGUAUGGGUCACAUCGCAG-3' (SEQ ID NO: 19).

Yet another embodiment of the invention is a method of enhancing the heregulin mediated activation of a HER2/HER3 receptor complex in a breast cancer cell comprising contacting the cell with an aptamer polynucleotide comprising the sequence of the A18 aptamer disclosed herein under conditions that allow the aptamer polynucleotide to interact with an extracellular portion of a HER3 polypeptide expressed by the cell such that heregulin mediated activation of a HER2/HER3 receptor is enhanced.

Another embodiment of the invention is a method for obtaining an aptamer capable of specifically binding to HER3 comprising following a SELEX methodology disclosed in Example 1B to obtain an aptamer capable of specifically adsorbing to HER3 is obtained. As the SELEX technology was used to identify aptamers from a randomized 49 nucleotide sequence, this technology is therefore also useful in the production of variants of these aptamers.

Another embodiment of the invention is a composition comprising an aptamer polynucleotide disclosed herein. In a preferred embodiment, the composition further comprises a pharmaceutically acceptable carrier. A specific embodiment of the invention is a composition comprising a polynucleotide comprising the sequence 5'-CAGCGAAAG-UUGCGUAUGGGUCACAUCGCAG-3' (SEQ ID NO: 19). A related embodiment is an isolated RNA-aptamer which binds to HER3 polypeptide and competitively inhibits binding of an aptamer disclosed herein.

Also contemplated are aptamer derivatives designed to have further advantageous properties such as a high in vivo and/or serum stability. Such derivatives includes for example S-oligonucleotides (phosphorothioate derivatives or S-oligos). S-oligos (nucleoside phosphorothioates) are isoelectronic analogs of an oligonucleotide (O-oligo) in which a nonbridging oxygen atom of the phosphate group is replaced by a sulfur atom. The S-oligos may be prepared by treatment of the corresponding O-oligos with 3H-1,2-benzodithiol-3-one-1,1-dioxide, which is a sulfur transfer reagent. See Iyer, R. P. et al, 1990, J. Org. Chem. 55:4693-4698; and Iyer, R. P. et al., 1990, J. Am. Chem. Soc. 112:1253-1254, the disclosures of which ate fully incorporated by reference herein. Moreover, modifications of internucleoside phosphates other than phosphorothioates may be used. Without comprising a complete listing, but as examples, one may mention methylphosphonates, phosphoroboronates, phosphoromorpholidates, butyl amidates, and peptide nucleic acid linkages. There may also be changes in the sugar ring, such as 2'-0 methyl or methoxy ethoxy additions to the 2'-ribosyl ring. There may also be modifications of the purine and pyrimidine bases themselves. In one illustrative embodiment, the aptamer comprises a nucleic acid sequence shown in FIG. 1, wherein the nucleic acid molecule further comprises a fluorine moiety or an amino moiety.

Yet another embodiment of the invention is the use of an A30 aptamer in the manufacture of a medicament for inhibiting the heregulin-dependent tyrosine phosphorylation of HER2 in a patient. A closely related embodiment is the use of an A30 aptamer in the manufacture of a medicament for inhibiting the heregulin induced growth response of cells in a patient. In a specific embodiment of this use, the patient has a tumor comprising tumor cells expressing receptors that bind the A30 aptamer. In a specific embodiment of this use, the patient has a cancer (e.g. a breast, ovarian or colon cancer) comprising cancer cells expressing receptors that bind the A30 aptamer.

The SELEX technology disclosed herein identified the nucleic acid aptamers from a randomized polynucleotide sequence. As is know in the art, this technology can be further utilized to make and select further variants of these sequences. Consequently, the SELEX technology enables the invention disclosed herein to encompass variants of the nucleic acid sequences disclosed herein which retain their biological activities. A preferred variant is one retains a biological activity such as the ability to bind HER3 and/or the inhibition or enhancement of heregulin mediated activities and is at least 80%, more preferably 90%, and most preferably a 95% nucleic acid sequence identity to a aptamer sequence disclosed herein (e.g. one shown in FIG. 1). A related embodiment of the invention is a nucleic acid sequence which is complementary and/or hybridizes under conditions of high stringency to the nucleic acid sequences disclosed herein. The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

As used herein, the terms "hybridize", "hybridizing", "hybridizes" and the like, used in the context of polynucleotides, are meant to refer to conventional hybridization conditions, preferably such as hybridization in 50% formamide/ 6×SSC/0.1% SDS/100 μg/ml ssDNA, in which temperatures for hybridization are above 37 degrees C. and temperatures for washing in 0.1×SSC/0.1% SDS are above 55 degrees C., and most preferably to stringent hybridization conditions. "Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands ate present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995). "Stringent conditions" or "high stringency conditions", as defined herein, may be identified by those that: (1) employ low ionic strength and high temperature for washing, for example 0.015 M sodium chloride/ 0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2× SSC (sodium chloride/sodium. citrate) and 50% formamide at 55° C., followed by a high-stringency wash consisting of 0.1×SSC containing EDTA at 55° C.

In the context of nucleic acid sequence comparisons, the term "identity" is used to express the percentage of nucleic acid residues at the same relative positions that are the same. Also in this context, the term "homology" is used to express the percentage of nucleic acid residues at the same relative positions that are either identical or are similar, using the conserved nucleic acid criteria of BLAST analysis, as is generally understood in the art. For example, % identity values may be generated by WU-BLAST-2 (Altschul et al., 1996, Methods in Enzymology 266:460-480.

The invention disclosed herein further provides articles of manufacture and kits which include reagents for performing for example, the methods disclosed herein. One illustrative embodiment is a kit comprising a nucleic acid molecule comprising the sequence 5'-CAGCGAAAG-UUGCGUAUGGGUCACAUCGCAG-3' (SEQ ID NO: 19) and methods for its use. Consequently, embodiment of the invention include kits and/or an article of manufacture containing materials (e.g. a HER3 aptamer polynucleotide disclosed herein) useful for the treatment of the disorders described above is provided. The article of manufacture comprises a container and a label Suitable containers include, for example, bottles, vials, syringes, and test tubes. The containers may be formed from a variety of materials such as glass or plastic. The container holds a HER3 aptamer composition which is effective for treating the condition and may have a sterile access port (for example the container may be an intravenous solution bag or a vial having a stopper pierceable by a hypodermic injection needle). The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

EXAMPLES

Example 1

Illustrative Materials and Methods

A. Production of HER3ECD:

HER3ECD was produced in S2 insect cells as described previously (see, e.g. Landgraf et al. (2000) Biochemistry 39, 8503-8511). In brief, the ECDs of HER3 were cloned into the pMT/BiP/V5-His A expression vector (Invitrogen, Carlsbad, Calif.), which carries a metallothionine promoter and a C-terminal hexa-His and V5-epitope tag. Inductions with 500 μM CuSO$_4$ were carried out for two days in 500 mL S2 media (Sigma, St. Louis, Mo.) with 10% fetal bovine serum at approximately 6×10⁶ cells/mL. The ECD was purified on a 5 mL Pharmacia HITRAP chelating column (Pharmacia, Picataway, N.J.).

B. SELEX

Single-stranded DNA templates for SELEX included 49 contiguous randomized positions flanked by constant regions (FIG. 1). The constant regions included targets for PCR primers and cloning sites (BamHI, EcoRI) as well as a T7 promoter. DNA templates (600 pmols) were transcribed in vitro (T7 RNA Polymerase Ribomax, Promega) and internally $^{32}$P labeled RNA was purified on an 8% denaturing polyacrylamide gel. Prior to each round of selection, the RNA was denatured in phosphate-buffered saline (PBS, 150 mM NaCl, 2.5 mM KCl, 81 mM $Na_2HPO_4$, and 14.7 mM $KH_2PO4$)) at 90° C. for 10 minutes and incubated on ice for 1 min.

A filter binding assay was employed for the first eight rounds of selection. The RNA pool was first counter-selected by passing through a HAWP filter with a 0.45 μm pore size. The counter-selected RNAs (400 pmol) were then incubated with HER3ECD at 37° C. for 10 minutes in binding buffer (10 mM HEPES pH 7.4, 100 mM NaCl, 2.5 mM $MgCl_2$). Over the course of selection the ratio of protein to RNA was gradually lowered from 4:1 to 1:2. Unbound aptamers were separated from protein-bound aptamers on a HWAP filters. After two washes with PBS, bound RNA was measured by scintillation counting of the filters and was retrieved by incubation in urea-citrate buffer (7 M urea; 0.1 M sodium citrate, pH 7.0; 3 mM EDTA) at 90° C. for 10 minutes.

A gel shift assay was employed in the last seven rounds of selection. RNA (10 pmol) was incubated with HER3ECD as described above and loaded on a 6% non-denaturing acrylamide gel. Gel electrophoresis was carried out at 4° C. The retarded band was isolated, and RNA was extracted from the gel in elution buffer (0.5 M NH4OAc, pH 7.5; 10 mM MgOAc, pH 7.0; 0.1% SDS; and 1 mM EDTA) overnight at room temperature.

For both selection methods, the RNA was subsequently reverse transcribed into cDNA by avian myeloblastosis virus reverse transcriptase at 42° C. for 1 hr in a buffer purchased from Promega. Finally, the cDNA was PCR amplified for the next round of selection. Individual clones were obtained by ligation of the PCR product into either pGEM4 or pGEM3Z vectors following digestion with EcoRI and BamHI.

C. Gel Mobility Shift Assay

For screening purposes, 8 pmol of internally labeled aptamer were incubated in binding buffer with 24 pmol of HER3ECD at 37° C. for 10 minutes and analyzed on 6% non-denaturing polyacrylamide gels as described above. Aptamers displaying substantial shift were reverse transcribed and sequenced. For subsequent analysis of A30 binding, internally labeled and unlabeled A30 was denatured at 90° C. for 2 min in PBS and cooled on ice for 1 min. A30 was incubated with HER3ECD in binding buffer for 10 min at 37° C. at the indicated concentrations and in the presence 0.5 μM tRNA and was analyzed by electrophoresis on a non-denaturing 6% polyacrylamide gel at 4° C. Were indicated, HER3ECD and heregulin were premixed at room temperature three minutes before the addition of A30.

D. Cellular Binding of A30:

MCF7 cells (ATCC) were grown to 70% confluency on 6 well plates and washed with ice cold PBS. Following the washes, cells were incubated at 4° C. with 1 mL ice cold PBS or PBS containing 200 nM heregulin. After four hours an equal volume of ice cold PBS containing two microliter internally $^{32}$P labeled A30 aptamer (80,000 cpm/μL), 20 μL RNAse inhibitor (20 units/μL), and varying concentrations of unlabeled aptamer were added. After four hours incubation, the supernatant was removed, and cells were washed three times with ice cold PBS. Displaced and bound radiolabeled aptamer was measured in duplicate.

E. Tyrosine Phosphorylation Assay:

MCF7 cells were seeded two days prior to the experiment in RPMI with 10% fetal bovine serum. Cells were serum starved 24 hours prior to stimulation. Following two washes with PBS, cells were stimulated with heregulin or heregulin plus different concentrations of aptamer in RPMI. After 15 minutes of stimulation at 37° C., cells were placed on ice and washed twice with ice cold PBS. Cells were lysed with mild lysis buffer (20 mM Tris 8.0, 137 mM NaCl, 1% Triton X-100, 10% glycerol, 5 mM EDTA, 1 mM sodium orthovanadate, 1 mM phenylmethyl-sulfinylfluoride, 1 μg/mL leupeptin, 1 μg/ml aprotinin). Lysates were either evaluated directly for tyrosine phosphorylation or were first subjected to immunoprecipitation in mild lysis buffer as described previously (see, e.g. Landgraf et al. (2000) Biochemistry 39, 8503-8511) using anti-HER2 antibody (Ab3, Oncogene) and ProteinA/G beads (Santa Cruz Biotech). Western blot analysis was done using an anti-phosphotyrosine antibody (4G10, Upstate) as the primary, and anti-mouse IgG-HRP conjugates (Upstate) as secondary antibody.

F. Cell Proliferation Assay:

MCF7 cells were seeded in 96 well plates (2500 cells/well) in RPMI, 2% fetal bovine serum, 2 units of RNAse inhibitor/ml and varying concentrations of heregulin and aptamer. After two days, cell growth was determined using an MTT/tetrazolium based assay (Promega). Cell growth was equated with the absorbance of converted and solubilized dye at 560 nm. All samples were determined in triplicate.

Example 2

Selection of RNA Aptamers that bind HER3ECD

HER3ECD has a molecular weight of 82 kD, which includes 12% carbohydrates (see, e.g. Landgraf et al. (2000) Biochemistry 39, 8503-8511), and represents an exceptionally large target for SELEX. At the high concentrations of HER3ECD requited for SELEX, the ECD is completely in its oligomeric state. Previous analysis suggests that the upper limit of self-association in solution are twelve copies of the ECD (see, e.g. Landgraf et al. (2000) Biochemistry 39, 8503-8511).

The analysis of 88 clones, obtained after 15 rounds of SELEX, identified 29 clones that gave reproducible positive results in gel mobility shift assays with HER3ECD. All 29 clones were sequenced. The sequences of six aptamers with good gel-shift properties ate disclosed herein. Beyond an apparent bias for adenine in the first half and uracil in the second half of the aptamers, we could not identify a consensus pattern. This apparent lack of a consensus among the 29 sequences could indicate insufficient sample sequences, several distinct bindings sites on the target, or both. Given the exceptionally large size of the ECD, the possibility of multiple target sites is plausible.

Depending on their site of binding, aptamers could interfere with receptor self-association, heterodimerization or ligand binding. We evaluated different aptamers for their ability to interfere with heregulin-induced tyrosine phosphorylation of HER2. While "low-affinity" binding of heregulin to HER3 has a $K_d$ of 2-8 nM, "high-affinity" binding to the HER3-HER2 heterodimer has a $K_d$ of ~$10^{-10}$M (see, e.g.

Tzahar et al. (1994) J Biol Chem 269, 25226-33) and results primarily in the phosphorylation of HER2. For the initial screen, we used an Ω-loop mutant of heregulin with reduced binding affinity. The Ω-loop is not essential for activity but multiple alanine mutations in this loop reduce the binding affinity towards HER3 (see, e.g. Jones et al. (1998) J Biol Chem 273, 11667-74). FIG. 2 shows the results obtained for the six aptamers shown in FIG. 1. Although all 29 of 88 aptamers were selected based on their ability to bind HER3ECD, they differ in their effect on receptor stimulation. Aptamer 19 shows little interference with heregulin-dependent activation while aptamer 30, and to a lesser extent 23 and 37, show inhibition. In contrast, aptamer 6 and 18 enhance heregulin dependent activation. A18 reproducibly caused a 24 (±4)% enhancement of heregulin stimulation in independent experiments. Further comparison of aptamer 18 and 30 revealed that neither elicits tyrosine phosphorylation by itself or displaces the other aptamer from its binding site on HER3ECD. Although the aptamers shown in FIG. 1 and 2 represent only a subset of all obtained sequences, the apparent qualitative differences in their activities and the lack of mutual competition of A18 and A30 are consistent with the assumption of at least two distinct binding sites. Because of the potency of A30 and the possibilities inherent in an aptamer with inhibitory properties, we focused on A30 for the remainder of this study.

Example 3

Specificity of A30

Given the high homology between HER3 and HER2, we next confirmed the specificity of A30 binding (FIG. 3). A gel-shift of A30 was observed only for HER3ECD (lane 3), but not for HER2-ECD (lane 2) or heregulin (lane 1). Furthermore, binding of A30 to HER3ECD cannot be inhibited by a 20-fold molar excess of tRNA (lane 4). Combined with the fact that the majority of aptamer sequences does not bind HER3ECD at all, these results indicate a high level of specificity in the interaction of HER3ECD and A30.

Example 4

Mode of Interaction Between A30 and HER3ECD

Figure 4:
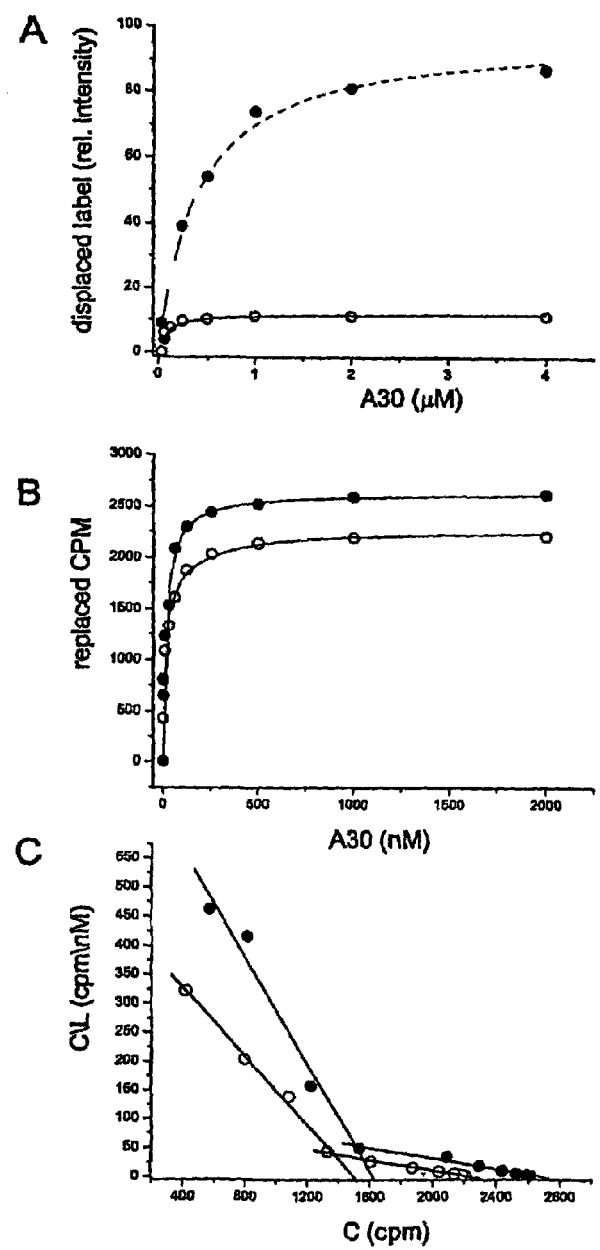
FIG. 4: Binding of A30 to HER3ECD and cellular HER3. A) Binding of A30 to purified HER3ECD, as determined by the replacement of radiolabeled A30 by unlabeled A30 in a gel-shift analysis, indicates a small number of high affinity binding sites in the absence of heregulin (○). Addition of heregulin (●) generates additional binding sites of lower affinity. B) Binding of A30 to cellular HER3 also shows an increase in binding sites upon addition of heregulin (●), though less pronounced than in solution. Binding data are shown as displaced labeled A30 (cpm) as a function of unlabeled A30. C) The Scatchard analysis of data shown in B) reveals a smaller increase in high affinity binding sites parallel with the larger increase in low affinity sites after addition of heregulin (●). C in this analysis represents displaced cpm, L represents the concentration of unlabeled A30 (nM).

Several lines of evidence provide evidence that the interaction of A30 with HER3ECD involves at least two different modes of binding. FIG. 4A shows A30 binding to the ECD in the presence and absence of heregulin, as determined by a gel shift assay. In the absence of heregulin, an apparent $K_d$ of 45 nM is obtained. Addition of heregulin has two consequences. The number of binding sites increases nine-fold, and the binding affinity decreases to an apparent $K_d$ of 400 nM. With respect to the heregulin-induced increase and dual mode of binding, we observed a similar, although less pronounced, effect for A30 binding to MCF7 cells (FIG. 4B+C). MCF7 cells endogenously express both HER3 and HER2. Overall, binding to MCF7 cells at 4° C. is tighter with a $K_d$ of 21 nM (±2.2) and 3.3 nM (±0.2) respectively for low and high affinity binding (FIG. 4C). The addition of heregulin results in an increase in the number of A30 binding sites (FIG. 4B), but this increase is relatively small (25% total 17% for low affinity and 8% for high affinity sites).

Across experiments, gelshifts of A30 with HER3ECD produce a set of three bands (A, B, C in FIG. 3 and 5), the ratio of which can differ based on the concentration of components as well as the particular batches of refolded A30. A direct comparison of binding with the same batch of A30 in the presence and absence of heregulin shows that bands that are not derived from A30 alone (Ctrl, lane 1 FIG. 5) are qualitatively the same in the presence and absence of heregulin (which contributes minimal changes in both the size and charges of the complex compared to A30). When the concentration of unlabeled A30 is increased, the faster migrating species (B and C) are more readily subject to competition. Upon addition of heregulin, increases in binding are primarily observed for the faster migrating species B and C.

We previously showed that HER3ECD has a high propensity to form oligomers in solution. Those oligomers dissociate in the presence of excess heregulin. To evaluate the binding preferences of A30 for the oligomeric versus the monomeric state of HER3ECD, we visualized HER3ECD as well as radiolabeled A30. Because of the close to neutral charges of the HER3ECD and HER3ECD-heregulin complex, both species are not well separated under gelshift conditions that are optimized for the highly charged and the fast migrating complexes with A30. A significant shift can be observed upon heregulin binding to HER3ECD in Phast gels®, probably as a result of the significantly higher current flow allowable in these systems. However, the nature of these gels makes Western blot analysis difficult. We therefore decided to visualize purified HER3ECD directly at high protein concentrations.

FIG. 6 shows the obtained shifts, visualized either through autoradiography of radiolabeled A30 or by coomassie staining. Radiolabeled A30 (0.3 nM) is present in all lanes. Lanes 3 and 4 show the partial gelshift of 2 µM HER3ECD with a 3 fold molar excess of heregulin, visualized by coomassie staining. Radiolabeled A30 binds to the oligomeric species of HER3ECD (lane 4 and 9). Under conditions when HER3ECD oligomers are in excess over A30 and disruption of HER3ECD oligomers by heregulin is only partial (lane 3 and 8). The simultaneous presence of oligomeric and monomeric species of HER3, detectable by coomassie staining, allows a direct comparison of A30 binding to both species. A30 preferentially binds the oligomeric species of HER3ECD. A small amount of an additional faster migrating species is visible on the autoradiography in both cases. Using a four-fold molar excess of A30 over HER3ECD results in three shifted species of HER3ECD, visible by direct coomassie staining (FIG. 6, lane 2). This comparison identifies the additional band (species c) in lanes 8 and 9 as a small portion of A30-shifted HER3ECD. The addition of heregulin does not alter this pattern. The assignment of species a, b and c in this experiment is based on the similarity in the pattern of bands with the gelshifts in FIG. 3 and 5 (lane 5). The distinction of lower and upper case letters reflects the fact that the equivalence of those bands has not been confined in light of the differences in the two gel systems.

Example 5

Inhibition of Tyrosine Phosphorylation and Growth Stimulation

Figure 8:
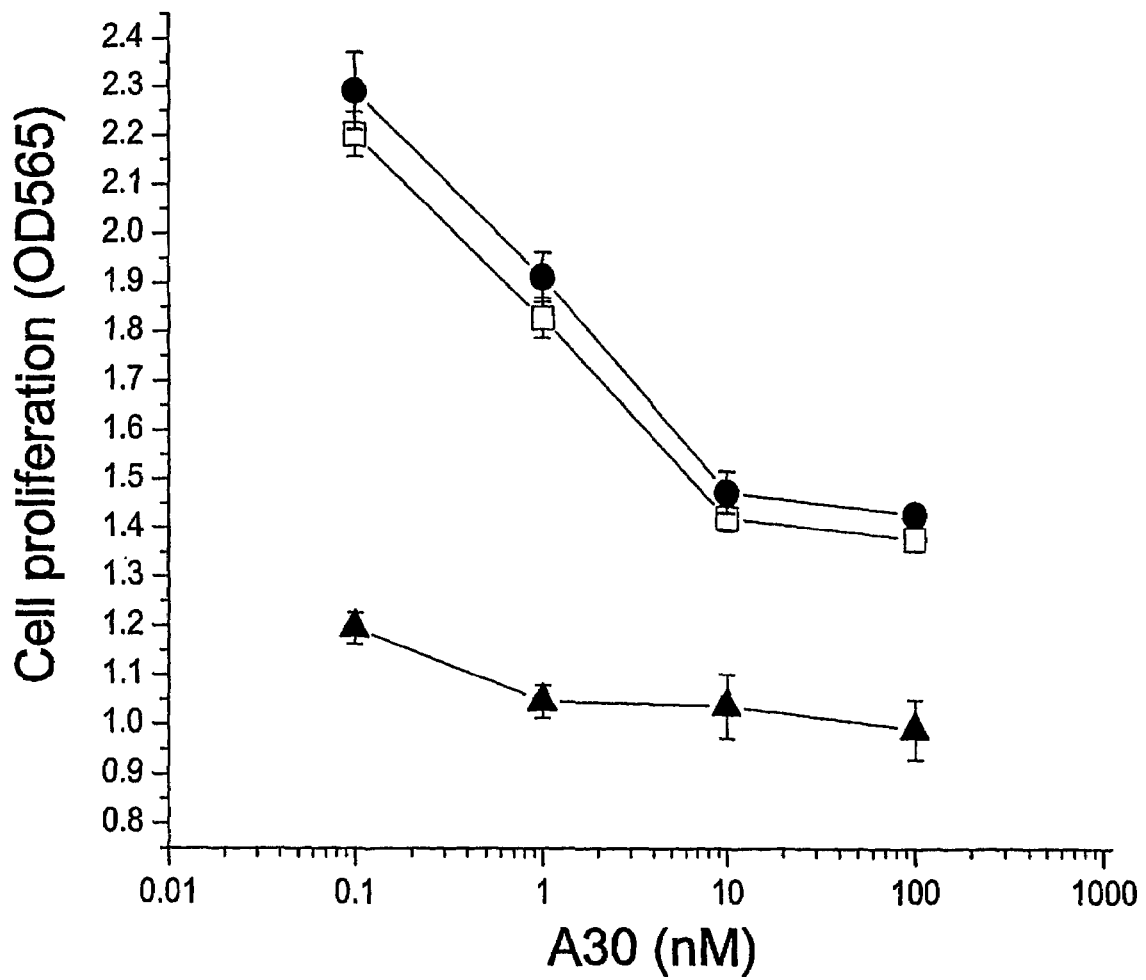
FIG. 8: Inhibition of heregulin induced cell growth in MCF7 cells. Cell growth (OD 560 after MTT assay) was measured as a function of A30 concentration (nM) in the presence of two different concentrations of wild type heregulin (no heregulin (▲), 5 nM (□) and 100 nM heregulin (●).

Next, we evaluated the ability of A30 to interfere with receptor activation by wild type heregulin. FIG. 7 shows HER2 tyrosine phosphorylation in MCF7 cells following stimulation by heregulin. Half-maximal inhibition of tyrosine phosphorylation occurs at a concentration around 10 nM A30 (FIG. 7a). In contrast, the activation of HER2 by EGF, which proceeds through hetetodimers of EGFR and HER2, is not inhibited by A30 (FIG. 7b). The low intensity of tyrosine phosphorylation of HER2 after stimulation by EGF is a reflection of the lower levels of EGFR (5000/cell) compared to HER2 (15,000) and HER3 (25,000) (see, e.g. Aguilar et al. (1999) Oncogene 18, 6050-62) and the fact that EGFR signaling proceeds only in part through heterodimers with HER2. To evaluate if the inhibition of tyrosine phosphorylation is reflected in a reduction in heregulin-specific growth stimulation, we incubated MCF7 cells in the presence of different concentrations of A30 and heregulin for two days (FIG. 8). The addition of A30 results in a 50% inhibition of heregulin-specific growth stimulation, even at high concentrations (100 nM) of heregulin. Half-maximal inhibition occurs at around 1 nM A30. The addition of A30 alone has little effect on the growth of MCF7 cells.

Throughout this application, various publications are referenced (e.g. Chen et al., Proc Natl Acad Sci USA. 2003;100 (16): 9226-31). The disclosures of these publications are hereby incorporated by reference herein in their entireties. The technology in this application is also related to U.S. application Ser. No. 10/207,498 filed Jul. 29, 2002, the contents of which are incorporated herein by reference.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE 1

Illustrative HER3, Heregulin and HER2 polynucleotide and polypeptide sequences:

1A. HER3 Polynucleotide Sequence

SEQ ID NO: 1
ATGAGGGCGAACGACGCTCTGCAGGTGCTGGGCTTGCTTTTCAGCCTGGC
CCGGGGCTCCGAGGTGGGCAACTCTCAGGCAGTGTGTCCTGGGACTCTGA
ATGGCCTGAGTGTGACCGGCGATGCTGAGAACCAATACCAGACACTGTAC
AAGCTCTACGAGAGGTGTGAGGTGGTGATGGGGAACCTTGAGATTGTGCT
CACGGGACACAATGCCGACCTCTCCTTCCTGCAGTGGATTCGAGAAGTGA
CAGGCTATGTCCTCGTGGCCATGAATGAATTCTCTACTCTACCATTGCCC
AACCTCCGCGTGGTGCGAGGGACCCAGGTCTACGATGGGAAGTTTGCCAT
CTTCGTCATGTTGAACTATAACACCAACTCCAGCCACGCTCTGCGCCAGC
TCCGCTTGACTCAGCTCACCGAGATTCTGTCAGGGGGTGTTTATATTGAG
AAGAACGATAAGCTTTGTCACATGGACACAATTGACTGGAGGGACATCGT
GAGGGACCGAGATGCTGAGATAGTGGTGAAGGACAATGGCGAAGCTGTC
CCCCCTGTCATGAGGTTTGCAAGGGGCGATGCTGGGGTCCTGGATCAGAA
GACTGCCAGACATTGACCAAGACCATCTGTGCTCCTCAGTGTAATGGTCA
CTGCTTTGGGCCCAACCCCAACCAGTGCTGCCATGATGAGTGTGCCGGGA
GCTGCTCAGGCCCTCAGGACACAGACTGCTTTGCCTGCCGGCACTTCAAT
GACAGTGGAGCCTGTGTACCTCGCTGTCCACAGCCTCTTGTCTACAACAA
GCTAACTTTCCAGCTGGAACCCAATCCCCACACCAAGTATCAGTATGGAG
GAGTTTGTGTAGCCAGCTGTCCCCATAACTTTGTGGTGGATCAAACATCC
TGTGTCAGGGCCTGTCCTCCTGACAAGATGGAAGTAGATAAAAATGGGCT
CAAGATGTGTGAGCCTTGTGGGGACTATGTCCCAAAGCCTGTGAGGGAA
CAGGCTCTGGGAGCCGCTTCCAGACTGTGGACTCGAGCAACATTGATGGA
TTTGTGAACTGCACCAAGATCCTGGGCAACCTGGACTTTCTGATCACCGG
CCTCAATGGAGACCCCTGGCACAAGATCCCTGCCCTGGACCCAGAGAAGC
TCAATGTCTTCCGGACAGTACGGGAGATCACAGGTTACCTGAACATCCAG
TCCTGGCCGCCCCACATGCACAACTTCAGTGTTTTTTCCAATTTGACAAC
CATTGGAGGCAGAAGCCTCTACAACCGGGGCTTCTCATTGTTGATCATGA
AGAACTTGAATGTCACATCTCTGGGCTTCCGATCCCTGAAGGAAATTAGT
GCTGGGCGTATCTATATAAGTGCCAATAGGCAGCTCTGCTACCACCACTC
TTTGAACTGGACCAAGGTGCTTCGGGGGCCTACGGAAGAGCGACTAGACA
TCAAGCATAATCGGCCGCGCAGAGACTGCGTGGCAGAGGGCAAAGTGTGT
GACCCACTGTGCTCCTCTGGGGGATGCTGGGGCCCAGGCCCTGGTCAGTG
CTTGTCCTGTCGAAATTATAGCCGAGGAGGTGTCTGTGTGACCCACTGCA
ACTTTCTGAATGGGGAGCCTCGAGCCTTTGCCCATGAGGCCGAATGCTTC
TCCTGCCACCCGGAATGCCAACCCATGGGGGGCACTGCCACATGCAATGG
CTCGGGCTCTGATACTTGTGCTCAATGTGCCCATTTTCGAGATGGGCCCC

ACTGTGTGAGCAGCTGCCCCCATGGAGTCCTAGGTGCCAAGGGCCCAATC
TACAAGTACCCAGATGTTCAGAATGAATGTCGGCCCTGCCATGAGAACTG
CACCCAGGGGTGTAAAGGACCAGAGCTTCAAGACTGTTTAGGACAAACAC
TGGTGCTGATCGGCAAAACCCATCTGACAATGGCTTTGACAGTGATAGCA
GGATTGGTAGTGATTTTCATGATGCTGGGCGGCACTTTTCTCTACTGGCG
TGGGCGCCGGATTCAGAATAAAAGGGCTATGAGGCGATACTTGGAACGGG
GTGAGAGCATAGAGCCTCTGGACCCCAGTGAGAAGGCTAACAAAGTCTTG
GCCAGAATCTTCAAAGAGACAGAGCTAAGGAAGCTTAAAGTGCTTGGCTC
GGGTGTCTTTGGAACTGTGCACAAAGGAGTGTGGATCCCTGAGGGTGAAT
CAATCAAGATTCCAGTCTGCATTAAAGTCATTGAGGACAAGAGTGGACGG
CAGAGTTTTCAAGCTGTGACAGATCATATGCTGGCCATTGGCAGCCTGGA
CCATGCCCACATTGTAAGGCTGCTGGGACTATGCCCAGGGTCATCTCTGC
AGCTTGTCACTCAATATTTGCCTCTGGGTTCTCTGCTGGATCATGTGAGA
CAACACCGGGGGGCACTGGGGCCACAGCTGCTGCTCAACTGGGGAGTACA
AATTGCCAAGGGAATGTACTACCTTGAGGAACATGGTATGGTGCATAGAA
ACCTGGCTGCCCGAAACGTGCTACTCAAGTCACCCAGTCAGGTTCAGGTG
GCAGATTTTGGTGTGGCTGACCTGCTGCCTCCTGATGATAAGCAGCTGCT
ATACAGTGAGGCCAAGACTCCAATTAAGTGGATGGCCCTTGAGAGTATCC
ACTTTGGGAAATACACACACCAGAGTGATGTCTGGAGCTATGGTGTGACA
GTTTGGGAGTTGATGACCTTCGGGGCAGAGCCCTATGCAGGGCTACGATT
GGCTGAAGTACCAGACCTGCTAGAGAAGGGGAGCGGTTGGCACAGCCCC
AGATCTGCACAATTGATGTCTACATGGTGATGGTCAAGTGTTGGATGATT
GATGAGAACATTCGCCCAACCTTTAAAGAACTAGCCAATGAGTTCACCAG
GATGGCCCGAGACCCACCACGGTATCTGGTCATAAAGAGAGAGAGTGGGC
CTGGAATAGCCCCTGGGCCAGAGCCCCATGGTCTGACAAACAAGAAGCTA
GAGGAAGTAGAGCTGGAGCCAGAACTAGACCTAGACCTAGACTTGGAAGC
AGAGGAGGACAACCTGGCAACCACCACACTGGGCTCCGCCCTCAGCCTAC
CAGTTGGAACACTTAATCGGCCACGTGGGAGCCAGAGCCTTTTAAGTCCA
TCATCTGGATACATGCCCATGAACCAGGGTAATCTTGGGGGTCTTGCCA
GGAGTCTGCAGTTTCTGGGAGCAGTGAACGGTGCCCCCGTCCAGTCTCTC
TACACCCAATGCCACGGGGATGCCTGGCATCAGAGTCATCAGAGGGGCAT
GTAACAGGCTCTGAGGCTGAGCTCCAGGAGAAAGTGTCAATGTGTAGAAG
CCGGAGCAGGAGCCGGAGCCCACGGCCACGCGGAGATAGCGCCTACCATT
CCCAGCGCCACAGTCTGCTGACTCCTGTTACCCCACTCTCCCCACCCGGG
TTAGAGGAAGAGGATGTCAACGGTTATGTCATGCCAGATACACACCTCAA
AGGTACTCCCTCCTCCCGGGAAGGCACCCTTTCTTCAGTGGGTCTCAGTT
CTGTCCTGGGTACTGAAGAAGAAGATGAAGATGAGGAGTATGAATACATG
AACCGGAGGAGAAGGCACAGTCCACCTCATCCCCCTAGGCCAAGTTCCCT
TGAGGAGCTGGGTTATGAGTACATGGATGTGGGGTCAGACCTCAGTGCCT
CTCTGGGCAGCACACAGAGTTGCCCACTCCACCCTGTACCCATCATGCCC
ACTGCAGGCACAACTCCAGATGAAGACTATGAATATATGAATCGGCAACG
AGATGGAGGTGGTCCTGGGGGTGATTATGCAGCCATGGGGGCCTGCCCAG
CATCTGAGCAAGGGTATGAAGAGATGAGAGCTTTTCAGGGGCCTGGACAT
CAGGCCCCCCATGTCCATTATGCCCGCCTAAAAACTCTACGTAGCTTAGA
GGCTACAGACTCTGCCTTTGATAACCCTGATTACTGGCATAGCAGGCTTT
TCCCCAAGGCTAATGCCCAGAGAACG

1B. HER3 Polypeptide Sequence

SEQ ID NO: 2
MRANDALQVLGLLFSLARGSEVGNSQAVCPGTLNGLSVTGDAENQYQTLY
KLYERCEVVMGNLEIVLTGHNADLSFLQWIREVTGYVLVAMNEFSTLPLP
NLRVVRGTQVYDGKFAIFVMLNYNTNSSHALRQLRLTQLTEILSGGVYIE
KNDKLCHMDTIDWRDIVRDRDAEIVVKDNGRSCPPCHEVCKGRCWGPGSE
DCQTLTKTICAPQCNGHCFGPNPNQCCHDECAGGCSGPQDTDCFACRHFN
DSGACVPRCPQPLVYNKLTFQLEPNPHTKYQYGGVCVASCPHNFVVDQTS
CVRACPPDKMEVDKNGLKMCEPCGGLCPKACEGTGSGSRFQTVDSSNIDG
FVNCTKILGNLDFLITGLNGDPWHKIPALDPEKLNVFRTVREITGYLNIQ
SWPPHMHNFSVFSNLTTIGGRSLYNRGFSLLIMKNLNVTSLGFRSLKEIS
AGRIYISANRQLCYHHSLNWTKVLRGPTEERLDIKHNRPRRDCVAEGKVC
DPLCSSGGCWGPGPGQCLSCPNYSRGGVCVTHCNFLNGEPREFAHEAECF
SCHPECQPMGGTATCNGSGSDTCAQCAHFRDGPHCVSSCPHGVLGAKGPI
YKYPDVQNECRPCHENCTQGCKGPELQDCLGQTLVLIGKTHLTMALTVIA
GLVVIFMMLGGTFLYWRGRRIQNKRAMRRYLERGESIEPLDPSEKANKVL
ARIFKETELRKLKVLGSGVFGTVHKGVWIPEGESIKIPVCIKVIEDKSGR
QSFQAVTDHMLAIGSLDHAHIVRLLGLCPGSSLQLVTQYLPLGSLLDHVR
QHRGALGPQLLLNWGVQIAKGMYYLEEHGMVHRNLAARNVLLKSPSQVQV
ADFGVADLLPPDDKQLLYSEAKTPIKWMALESIHFGKYTHQSDVWSYGVT
VWELMTFGAEPYAGLRLAEVPDLLEKGERLAQPQICTIDVYMVMVKCWMI
DENIRPTFKELANEFTRMARDPPRYLVIKRESGPGIAPGPEPHGLTNKKL
EEVELEPELDLDLDLEAEEDNLATTTLGSALSLPVGTLNRPRGSQSLLSP
SSGYMPMNQGNLGGSCQESAVSGSSERCPRPVSLHPMPRGCIASESSEGH
VTGSEAELQEKVSMCRSRSRSRSPRPRGDSAYHSQRHSLLTPVTPLSPPG
LEEEDVNGYVMPDTHLKGTPSSREGTLSSVGLSSVLGTEEEDEDEEYEYM

TABLE 1-continued

Illustrative HER3, Heregulin and HER2 poly-
nucleotide and polypeptide sequences:

NRRRRHSPPHPPRPSSLEELGYEYMDVGSDLSASLGSTQSCPLHPVPIMP
TAGTTPDEDYEYMNRQRDGGGPGGDYAAMGACPASEQGYEEMRAFQGPGH
QAPHVHYARLKTLRSLEATDSAFDNPDYWHSRLFPKANAQRT

1C. Heregulin Polynucleotide Sequence

SEQ ID NO: 3
ATGTCCGAGCGCAAAGAAGGCAGAGGCAAAGGGAAGGGCAAGAAGAAGGA
GCGAGGCTCCGGCAAGAAGCCGGAGTCCGCGGCGGGCAGCCAGAGCCCAG
CCTTGCCTCCCCAATTGAAAGAGATGAAAAGCCAGGAATCGGCTGCAGGT
TCCAAACTAGTCCTTCGGTGTGAAACCAGTTCTGAATACTCCTCTCTCAG
ATTCAAGTGGTTCAAGAATGGGAATGAATTGAATCGAAAAAACAAACCAC
AAAATATCAAGATACAAAAAAGCCAGGGAAGTCAGAACTTCAGCATTAAG
AAAGCATCACTGGCTGATTCTGGAGAGTATATGTGCAAAGTGATCAGCAA
ATTAGGAAATGACAGTGCCTCTGCCAATATCACCATCGTGGAATCAAACG
AGATCATCACTGGTATGCCAGCCTCAACTGAAGGAGCATATGTCTTCA
GAGTCTCCCATTAGAAATATCAGTATCCACAGAAGGAGCAAATACTTCTTC
ATCTACATCTACATCCACCACTGGGACAAGCCATCTTGTAAAATGTGCGG
AGAAGGAGAAACTTTCTGTGTGAATGGAGGGGAGTGCTTCATGGTGAAA
GACCTTTCAAACCCCTCGAGATACTTGTGCAAGTGCCCAATGAGTTTAC
TGGTGATCGCTGCCAAAACTACGTAATGGCCAGCTTCTACAAGCATCTTG
GGATTGAATTTATGGAGGCGGAGGAGCTGTACCAGAGAGAGTGCTGACC
ATAACCGGCATCTGCATCGCCCTCCTTGTGGTCGGCATCATGTGTGTGGT
GGCCTACTGCAAAACCAAGAAACAGCGGAAAAAGCTGCATGACCGTCTTC
GGCAGAGCCTTCGGTCTGAACGAAACAATATGATGAACATTGCCAATGGG
CCTCACCATCCTAACCCACCCCCGAGAATGTCCAGCTGGTGAATCAATA
CGTATCTAAAAACGTCATCTCCAGTGAGCATATTGTTGAGAGAGAAGCAG
AGACATCCTTTTCCACCAGTCACTATACTTCCACAGCCCATCACTCCACT
ACTGTCACCCAGACTCCAGCCACAGCTGGAGCAACGGACACACTGAAAG
CATCCTTTCCGAAAGCCACTCTGTAATCGTGATGTCATCCGTAGAAACA
GTAGGCACAGCAGCCCAACTGGGGGCCAAGAGGACGTCTTAATGGCACA
GGAGGCCCTCGTGAATGTAACAGCTTCCTCAGGCATGCCAGAGAAACCCC
TGATTCCTACCGAGACTCTCCTCATAGTGAAAGGTATGTGTCAGCCATGA
CCACCCGGCTCGTATGTCACCTGTAGATTTCCACAGCCAAGCTCCCCC
AAATCGCCCCCTTCGGAAATGTCTCCACCCGTGTCCAGCATGACGGTGTC
CATGCCTTCCATGCGGTCAGCCCCTTCATGAAGAAGAGAGACCTCTAC
TTCTCGTGACACCACCAAGGCTGCGGGAGAAGAAGTTTGACCATCACCCT
CAGCAGTTCAGCTCCTTCCACCACAACCCCGCGCATGACAGTAACAGCCT
CCCTGCTAGCCCCTTGAGGATAGTGGAGGATGAGGATGAAAACGACCC
AAGAGTACGAGCCAGCCCAAGAGCCTGTTAAGAAACTCGCCAATAGCCGG
CGGGCCAAAAGAACCAAGCCCAATGGCCACATTGCTAACAGATTGGAAGT
GGACAGCAACACAAGCTCCCAGACAGTAACTCAGAGAGTGAACAAGAAG
ATGAAAGAGTAGGTGAAGATACGCCTTTCCTGGGACATACAGAACCCCTG
GCAGCCAGTCTTGAGGCAACACCTGCCTTCCGCCTGGCTGACAGCAGGAC
TAACCCAGCAGGCCGCTTCTCGACACAGGAAGAAATCCAGGCCAGGCTGT
CTAGTGTAATTGCTAACCAAGACCCTATTGCTGTA

1D. Heregulin Polypeptide Sequence

SEQ ID NO: 4
MSERKEGRGKGKGKKKERGSGKKPESAAGSQSPALPPRLKEMKSQESAAG
SKLVLRCETSSEYSSLRFKWFKNGNELNRKNKPQNIKIQKKPGKSELRIN
KASLADSGEYMCKVISKLGNDSASANITIVESNEIIGMPASTEGAYVSS
ESPIRISVSTEGANTSSSTSTSTTGTSHLVKCAEKEKTFCVNGGECFMVK
DLSNPSRYLCKCPNEFTGDRCQNYVMASFYKHLGIEFMEAEELYQKRVLT
ITGICIALLVVGIMCVVAYCKTKKQRKKLHDRLRQSLRSERNNMMNIANG
PHHPNPPPENVQLVNQYVSKNVISSEHIVEREAETSFSTSHYTSTAHHST
TVTQTPSHSWSNGNTESILSESHSVIVMSSVENSRHSSPTGGPRGRLNGT
GGPRECNSFLRHARETPDSYRDSPHSERYVSAMTTPARMSPVDFHTPSSP
KSPPSEMSPPVSSMTVSMPSMAVSPFMEEEERPLLLVTPPRLREKKFDHHP
QQFSSPHHNPAHDSNSLPASPLRIVEDEEYETTQEYEPAQEPVKKLANSR
RAKRTKPNGHIANRLEVDSNTSSQSSNSESETEDERVGEDTPFLGIQNPL
AASLEATPAFRLADSRTNPAGRFSTQEEIQARLSSVIANQDPIAV

1E. HER2 Polynucleotide Sequence

SEQ ID NO: 5
ATGGAGCTGGCGGCCTTGTGCCGCTGGGGGCTCCTCCTCGCCCTCTTGCC
CCCCGGAGCCGCGAGCACCCAAGTGTGCACCGGCACAGACATGAAGCTGC
GGCTCCCTGCCAGTCCCGAGACCCACCTGGACATGCTCCGCCACCTCTAC
CAGGGCTGCCAGGTGGTGCAGGGAAACCTGGAACTCACCTACCTGCCCA
CAATGCCAGCCTGTCCTTCCTGCAGGATATCCAGGAGGTGCAGGGCTACG
TGCTCATCGCTCACAACCAAGTGAGGCAGGTCCCACTGCAGAGGCTGCGG
ATTGTGCGAGGCACCCAGCTCTTTGAGGACAACTATGCCCTGGCCGTGCT
AGACAATGGAGACCCGCTGAACAATACCACCCCTGTCACAGGGGCCTCC
CAGGAGGCCTGCGGGAGCTGCAGCTTGAAGCCTCACAGAGATCTTGAAA

GGAGGGGTCTTGATCCAGCGGAACCCCCAGCTCTGCTACCAGGACACGAT
TTTGTGGAAGGACATCTTCCACAAGAACAACCAGCTGGCTCTCACACTGA
TAGACACCAACCGCTCTCGGGCCTGCCACCCCTGTTCTCCGATGTGTAAG
GGCTCCCGCTGCTGGGGAGAGAGTTCTGAGGATTGTCAGAGCCTGACGCG
CACTGTCTGTGCCGGTGGCTGTGCCCGCTGCAAGGGGCCACTGCCCACTG
ACTGCTGCCATGAGCAGTGTGCTGCCGGCTGCACGGGCCCCAAGCACTCT
GACTGCCTGGCCTGCCTCCACTTCAACCACAGTGGCATCTGTGAGCTGCA
CTGCCCAGCCCTGGTCACCTACAACACAGACACGTTTGAGTCCATGCCCA
ATCCTGAGGGCCGGTATACATTCGGCGCCCAGCTGTGTGACTGCCTGTCCC
TACAACTACCTTTCTACGGACGTGGGATCCTGCACCCTCGTCTGCCCCCT
GCACAACCAAGAGGTGACAGCAGAGGATGGAACACAGCGGTGTGAGAAGT
GCAGCAAGCCCTGTGCCCGAGTGTGCTATGGTCTGGGCATGGAGCACTTG
CGAGAGGTGAGGGCAGTTACCAGTGCCAATATCCAGGAGTTTGCTGGCTG
CAAGAAGATCTTTGGGAGCCTGGCATTTCTGCCGGAGAGCTTTGATGGGG
ACCCAGCCTCCAACACTGCCCCGCTCCAGCCAGAGCAGCTCCAAGTGTTT
GAGACTCTGGAAGAGATCACAGGTTACCTATACATCTCAGCATGGCCGGA
CAGCCTGCCTGACCTCAGCGTCTTCCAGAACCTGCAAGTAATCCGGGGAC
GAATTCTGCACAATGGCGCCTACTCGCTGACCCTGCAAGGGCTGGGCATC
AGCTGGCTGGGGCTGCGCTCACTGAGGGAACTGGGCAGTGGACTGGCCCT
CATCCACCATAACACCCACCTCTGCTTCGTGCACACGGTGCCCTGGGACC
AGCTCTTTCGGAACCCGCACCAAGCTCTGCTCCACACTGCCAACCGGCCA
GAGGACGAGTGTGTGGGCGAGGGCCTGGCCTGCCACCAGCTGTGCGCCCA
AGGGCACTGCTGGGGTCCAGGGCCACCCAGTGTGTCAACTGCAGCCAGT
TCCTTCGGGGCCAGGAGTGCGTGGAGGAATGCCGAGTACTGCAGGGGCTC
CCCAGGGAGTATGTGAATGCCAGGCACTGTTTGCCGTGCCACCCTGAGTG
TCAGCCCCAGAATGGCTCAGTGACCTGTTTTGGACCGGAGGCTGACCAGT
GTGTGGCCTGTGCCCACTATAAGGACCCTCCCTTCTGCGTGGCCCGCTGC
CCCAGCGGTGTGAAACCTGACCTCTCCTACATGCCCATCTGGAAGTTTCC
AGATGAGGAGGGCGCATGCCAGCCTTGCCCCATCAACTGCACCCACTCC
TGTGTGGACCTGGATGACAAGGGCTGCCCCGCCGAGCAGAGAGCCAGCCCT
CTGACGTCCATCGTCTCTGCCGTGGTTGGCATTCTGCTGGTCGTGGTCTT
GGGGGTGGTCTTTGGGATCCTCATCAAGCGACGGCAGCAGAAGATCCGGA
AGTACACGATGCGGAGACTGCTGCAGGAAACGGAGCTGGTGGAGCCGCTG
ACACCTAGCGGAGCGATGCCCAACCAGGCGCAGATGCGGATCCTGAAAGA
GACGGAGCTGAGGAAGGTGAAGGTGCTTGGATCTGCGCTTTTGGCACAG
TCTACAAGGGCATCTGGATCCCTGATGGGGAGAATGTGAAAATTCCAGTG
GCCATCAAAGTGTTGAGGGAAAACACATCCCCCAAAGCCAACAAAGAAAT
CTTAGACGAAGCATACGTGATGGCTGGTGTTGGGCTCCCATATGTCTCCC
GCCTTCTGGGCATCTGCCTGACATCCACGGTGCAGCTGGTGACACAGCTT
ATGCCCTATGGCTGCCTCTTAGACCATGTCCGGGAAAACCGCGGACGCCT
GGGCTCCCAGGACCTGCTGAACTGGTGTATGCAGATTGCCAAGGGGATGA
GCTACCTGGAGGATGTGCGGCTCGTACACAGGGACTTGGCCGCTCGGAAC
GTGCTGGTCAAGAGTCCCAACCATGTCAAAATTACAGACTTCGGGCTGGC
TCGGCTGCTGGACATTGACGAGACAGAGTACCATGCAGATGGGGGCAAGG
TGCCCATCAAGTGGATGGCGCTGGAGTCCATTCTCCGCCGGCGGTTCACC
CACCAGAGTGATGTGTGGAGTTATGGTGTGACTGTGTGGGAGCTGATGAC
TTTTGGGGCCAAACCTTACGATGGGATCCCAGCCCGGGAGATCCCTGACC
TGCTGGAAAAGGGGGAGCGGCTGCCCCAGCCCCCCATCTGCACCATTGAT
GTCTACATGATCATGGTCAAATGTTGGATGATTGACTCTGAATGTCGGCC
AAGATTCCGGGAGTTGGTGTCTGAATTCTCCCGCATGGCCAGGGACCCCC
AGCGCTTTGTGGTCATCCAGAATGAGGACTTGGGCCCAGCCAGTCCCTTG
GACAGCACCTTCTACCGCTCACTGCTGGAGGACGATGACATGGGGGACCT
GGTGGATGCTGAGGAGTATCTGGTACCCCAGCAGGGCTTCTTCTGTCCAG
ACCCTGCCCCGGGCGCTGGGGGCATGGTCCACCACAGGCACCGCAGCTCA
TCTACCAGGAGCTGCGGTGGGACCTGACATAGGGCTGGAGCCCTCTGA
AGAGGAGGCCCCAGGTCTCCACTGGACACCCTCCGAAGGGGCTGGCTCCG
ATGTATTTGATGGTGACCTGGGAATGGGGGCAGCCAAGGGGCTGCAAAGC
CTCCCCACACATGACCCCAGCCCTCTACAGCGGTACAGTGAGGACCCCAC
AGTACCCCTGCCCTCTGAGACTGATGGCTACGTTGCCCCCCTGACCTGCA
GCCCCCAGCCTGAATATGTGAACCAGCCAGATGTTCGGCCCCAGCCCCCT
TCGCCCCGAGAGGGCCCTCTGCCTGCTGCCCGACCTGCTGGTGCCACTCT
GGAAAGGGCCAAGACTCTCTCCCCAGGGAAGAATGGGGTCGTCAAAGACG
TTTTTGCCTTTGGGGGTGCCGTGGAGAACCCCGAGTACTTGACACCCCAG
GGAGGAGCTGCCCCTCAGCCCCACCCTCCTCCTGCCTTCAGCCCAGCCTT
CGACAACCTCTATTACTGGGACCAGGACCCACCAGAGCGGGGGGCTCCAC
CCAGCACCTTCAAAGGGACACACGGCAGAGAACCCAGAGTACCTGGGT
CTGGACGTGCCAGTG

1F. HER2 Polypeptide Sequence

SEQ ID NO: 6
MELAALCRWGLLLALLPPGAASTQVCTGTDMKLRLPASPETHLDMLRHLY
QGCQVVQGNLELTYLPTNASLSFLQDIQEVQGYVLIAHNQVRQVPLQRLR
IVRGTQLFEDNYALAVLDNGDPLNNTTPVTGASPGGLRELQLRSLTEILK
GGVLIQRNPQLCYQDTILWKDIFHKNNQLALTLIDTNRSRACHPCSPMCK
GSRCWGESSEDCQSLTRTVCAGGCARCKGPLPTDCCHEQCAAGCTGPKHS

TABLE 1-continued

Illustrative HER3, Heregulin and HER2 poly-
nucleotide and polypeptide sequences:

DCLACLHFNHSGICELHCPALVTYNTDTFESMPNPEGRYTFGASCVTACP
YNYLSTDVGSCTLVCPLHNQEVTAEDGTQRCEKCSKPCARVCYGLGMEHL
REVRAVTSANIQEFAGCKKIFGSLAFLPESFDGDPASNTAPLQPEQLQVF
ETLEEITGYLYISAWPDSLPDLSVFQNLQVIRGRILHNGAYSLTLQGLGI
SWLGLRSLRELGSGLALIHHNTHLCFVHTVPWDQLFRNPHQALLHTANRP
EDECVGEGLACHQLCARGHCWGPGPTQCVNCSQFLRGQECVEECRVLQGL
PREYVNARHCLPCHPECQPQNGSVTCFGPEADQCVACAHYKDPPFCVARC
PSGVKPDLSYMPIWKFPDEEGACQPCPINCTHSCVDLDDKGCPAEQRASP
LTSIVSAVVGILLVVVLGVVFGILIKRRQQKIRKYTMRRLLQETELVEPL
TPSGAMPNQAQMRILKETELRKVKVLGSGAFGTVYKGIWIPDGENVKIPV
AIKVLRENTSPKANKEILDEAYVMAGVGSPYVSRLLGICLTSTVQLVTQL

TABLE 1-continued

Illustrative HER3, Heregulin and HER2 poly-
nucleotide and polypeptide sequences:

MPYGCLLDHVRENRGRLGSQDLLNWCMQIAKGMSYLEDVRLVHRDLAARN
VLVKSPNHVKITDFGLARLLDIDETEYHADGGKVPIKWMALESILRRRFT
HQSDVWSYGVTVWELMTFGAKPYDGIPAREIPDLLEKGERLPQPPICTID
VYMIMVKCWMIDSECRPRFRELVSEFSRMARDPQRFVVIQNEDLGPASPL
DSTFYRSLLEDDDMGDLVDAEEYLVPQQGFFCPDPAPGAGGMVHHRHRSS
STRSGGGDLTLGLEPSEEEAPRSPLAPSEGAGSDVFDGDLGMGAAKGLQS
LPTHDPSPLQRYSEDPTVPLPSETDGYVAPLTCSPQPEYVNQPDVRPQPP
SPREGPLPAARPAGATLERAKTLSPGKNGVVKDVFAFGGAVENPEYLTPQ
GGAAPQPHPPPAFSPAFDNLYYWDQDPPERGAPPSTFKGTPTAENPEYLG
LDVPV

What is claimed is:

1. An isolated nucleic acid molecule that binds HER3 polypeptide (SEQ ID NO: 2), wherein the nucleic acid molecule comprises the sequence: 5'-CAGCGAAAG-UUGCGUAUGGGUCACAUCGCAG-3' (SEQ ID NO: 19).

2. The nucleic acid molecule of claim 1, wherein the nucleic acid molecule comprises the sequence shown in SEQ ID NO: 7, SEQ ID NO: 12, SEQ ID NO: 15, SEQ ID NO: 16, SEQ ID NO: 17 or SEQ ID NO: 18.

3. The nucleic acid molecule of claim 1, wherein the nucleic acid molecule further comprises a fluorine moiety or an amino moiety.

4. The nucleic acid molecule of claim 1, wherein the nucleic acid molecule of SEQ ID NO: 16 forms a hairpin loop structure:

5. The nucleic acid molecule of claim 1, wherein the nucleic acid molecule is labeled with a detectable marker.

6. A vector comprising the nucleic acid molecule of claim 1, wherein uridine (U) is replaced with thymidine (T).

7. A host cell comprising the vector of claim 6.

8. A method of binding a nucleic acid molecule comprising the sequence 5'-CAGCGAAAGUUGCGUAUGGGUCA-CAUCGCAG-3' (SEQ ID NO: 19) to a HER3 polypeptide encoded by a polynucleotide of SEQ ID NO: 1 comprising combining the nucleic acid molecule and the HER3 polypeptide for a time and under conditions effective to allow the nucleic acid molecule to bind to the HER3 polypeptide such that said binding occurs.

9. The method of claim 8, wherein the nucleic acid molecule is combined with HER3 polypeptide expressed on the

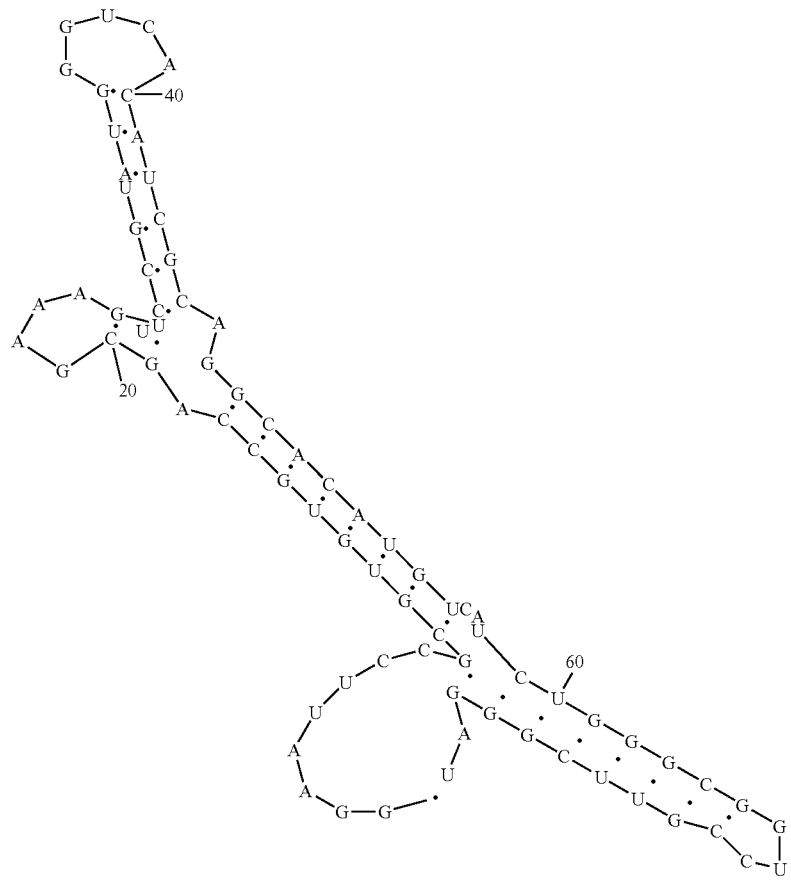

surface of a human cell and the method further comprises the step of examining the affinity of the nucleic acid molecule for the HER3 polypeptide.

10. The method of claim 8, wherein the nucleic acid molecule is combined with HER3 polypeptide expressed on the surface of a human cell and the method further comprises the step of examining the number of nucleic acid molecule binding sites in the HER3 polypeptide.

11. The method of claim 8, wherein the nucleic acid molecule is combined with HER3 polypeptide expressed on the surface of a human cell that further expresses HER2 polypeptide (SEQ ID NO: 6) and the method further comprises examining the human cell for evidence of said binding, wherein the inhibition of heregulin (SEQ ID NO: 4) induced tyrosine phosphorylation of HER2 in the human cell provides evidence of said binding.

12. The method of claim 8, wherein the nucleic acid molecule is combined with HER3 polypeptide expressed on the surface of a human cell that further expresses HER2 polypeptide (SEQ ID NO: 6) and the method further comprises examining the human cell for evidence of said binding, wherein the inhibition of heregulin (SEQ ID NO: 4) induced growth in the human cell provides evidence of said binding.

13. The method of claim 8, further comprising examining the HER3 polypeptide for evidence of said binding via a native gel mobility shift assay.

14. The method of claim 8, further comprising examining the affinity of the nucleic acid molecule for the HER3 polypeptide.

15. The method of claim 8, further comprising examining the number of binding sites for the nucleic acid molecule present on the HER3 polypeptide.

16. The method of claim 8, wherein the nucleic acid molecule and the HER3 polypeptide are combined in vitro.

17. The method of claim 8, wherein the nucleic acid molecule and the HER3 polypeptide are combined in vivo.

18. The method of claim 8, wherein the nucleic acid molecule is labeled with a detectable marker.

19. A kit comprising the nucleic acid molecule of claim 1 and written material describing methods for its use.

\* \* \* \* \*

UNITED STATES PATENT AND TRADEMARK OFFICE
CERTIFICATE OF CORRECTION

PATENT NO. : 7,531,649 B2  Page 1 of 1
APPLICATION NO. : 10/563888
DATED : May 12, 2009
INVENTOR(S) : Chi-Hong B. Chen et al.

It is certified that error appears in the above-identified patent and that said Letters Patent is hereby corrected as shown below:

Column 1

Lines 13-18 please delete

"STATEMENT OF GOVERNMENT SUPPORT

This invention was made in part with United States government support under national Institutes of Health Grant No. GM-21199. The Government has certain rights in the invention."

and, insert

--STATEMENT REGARDING FEDERALLY SPONSORED RESEARCH OR DEVELOPMENT

This invention was made with Government support of Grant Nos. AI009619 and GM021199 awarded by the National Institutes of Health. The Government has certain rights in this invention.--

Signed and Sealed this

Twentieth Day of July, 2010

David J. Kappos
*Director of the United States Patent and Trademark Office*

SEQUENCE LISTING

<160> NUMBER OF SEQ ID NOS: 20

<210> SEQ ID NO 1
<211> LENGTH: 4026
<212> TYPE: DNA
<213> ORGANISM: Homo sapiens

<400> SEQUENCE: 1

| | | | | | |
|---|---|---|---|---|---|
| atgagggcga | acgacgctct | gcaggtgctg | ggcttgcttt | tcagcctggc | ccggggctcc | 60 |
| gaggtgggca | actctcaggc | agtgtgtcct | gggactctga | atgcctgag | tgtgaccggc | 120 |
| gatgctgaga | accaatacca | gacactgtac | aagctctacg | agaggtgtga | ggtggtgatg | 180 |
| gggaaccttg | agattgtgct | cacgggacac | aatgccgacc | tctccttcct | gcagtggatt | 240 |
| cgagaagtga | caggctatgt | cctcgtggcc | atgaatgaat | tctctactct | accattgccc | 300 |
| aacctccgcg | tggtgcgagg | gacccaggtc | tacgatggga | agtttgccat | cttcgtcatg | 360 |
| ttgaactata | caccaactc | cagccacgct | ctgcgccagc | tccgcttgac | tcagctcacc | 420 |
| gagattctgt | caggggtgt | ttatattgag | aagaacgata | agctttgtca | catggacaca | 480 |
| attgactgga | gggacatcgt | gagggaccga | gatgctgaga | tagtggtgaa | ggacaatggc | 540 |
| agaagctgtc | cccctgtca | tgaggtttgc | aagggcgat | gctggggtcc | tggatcagaa | 600 |
| gactgccaga | cattgaccaa | gaccatctgt | gctcctcagt | gtaatggtca | ctgctttggg | 660 |
| cccaaccca | accagtgctg | ccatgatgag | tgtgccgggg | gctgctcagg | ccctcaggac | 720 |
| acagactgct | tgcctgccg | gcacttcaat | gacagtggag | cctgtgtacc | tcgctgtcca | 780 |
| cagcctcttg | tctacaacaa | gctaactttc | cagctggaac | ccaatcccca | caccaagtat | 840 |
| cagtatggag | gagtttgtgt | agccagctgt | ccccataact | tgtggtgga | tcaaacatcc | 900 |
| tgtgtcaggg | cctgtcctcc | tgacaagatg | gaagtagata | aaaatgggct | caagatgtgt | 960 |
| gagccttgtg | ggggactatg | tcccaaagcc | tgtgagggaa | caggctctgg | gagccgcttc | 1020 |
| cagactgtgg | actcgagcaa | cattgatgga | tttgtgaact | gcaccaagat | cctgggcaac | 1080 |
| ctggactttc | tgatcaccgg | cctcaatgga | gacccctggc | acaagatccc | tgccctggac | 1140 |
| ccagagaagc | tcaatgtctt | ccggacagta | cgggagatca | caggttacct | gaacatccag | 1200 |
| tcctggccgc | cccacatgca | caacttcagt | gttttttcca | atttgacaac | cattggaggc | 1260 |
| agaagcctct | acaaccgggg | cttctcattg | ttgatcatga | agaacttgaa | tgtcacatct | 1320 |
| ctgggcttcc | gatccctgaa | ggaaattagt | gctgggcgta | tctatataag | tgccaatagg | 1380 |
| cagctctgct | accaccactc | tttgaactgg | accaaggtgc | ttcgggggcc | tacggaagag | 1440 |

-continued

```
cgactagaca tcaagcataa tcggccgcgc agagactgcg tggcagaggg caaagtgtgt   1500
gacccactgt gctcctctgg gggatgctgg ggcccaggcc ctggtcagtg cttgtcctgt   1560
cgaaattata gccgaggagg tgtctgtgtg acccactgca actttctgaa tggggagcct   1620
cgagaatttg cccatgaggc cgaatgcttc tcctgccacc cggaatgcca acccatgggg   1680
ggcactgcca catgcaatgg ctcgggctct gatacttgtg ctcaatgtgc ccattttcga   1740
gatgggcccc actgtgtgag cagctgcccc catggagtcc taggtgccaa gggcccaatc   1800
tacaagtacc cagatgttca gaatgaatgt cggccctgcc atgagaactg cacccagggg   1860
tgtaaaggac cagagcttca agactgttta ggacaaacac tggtgctgat cggcaaaacc   1920
catctgacaa tggctttgac agtgatagca ggattggtag tgattttcat gatgctgggc   1980
ggcacttttc tctactggcg tgggcgccgg attcagaata aaagggctat gaggcgatac   2040
ttggaacggg gtgagagcat agagcctctg accccagtg agaaggctaa caaagtcttg   2100
gccagaatct tcaaagagac agagctaagg aagcttaaag tgcttggctc gggtgtcttt   2160
ggaactgtgc acaaaggagt gtggatccct gagggtgaat caatcaagat tccagtctgc   2220
attaaagtca ttgaggacaa gagtggacgg cagagttttc aagctgtgac agatcatatg   2280
ctggccattg gcagcctgga ccatgcccac attgtaaggc tgctgggact atgcccaggg   2340
tcatctctgc agcttgtcac tcaatatttg cctctgggtt ctctgctgga tcatgtgaga   2400
caacaccggg gggcactggg gccacagctg ctgctcaact ggggagtaca aattgccaag   2460
ggaatgtact accttgagga acatggtatg gtgcatagaa acctggctgc ccgaaacgtg   2520
ctactcaagt cacccagtca ggttcaggtg gcagattttg gtgtggctga cctgctgcct   2580
cctgatgata agcagctgct atacagtgag gccaagactc caattaagtg gatggccctt   2640
gagagtatcc actttgggaa atacacacac cagagtgatg tctggagcta tggtgtgaca   2700
gtttgggagt tgatgacctt cggggcagag ccctatgcag ggctacgatt ggctgaagta   2760
ccagacctgc tagagaaggg ggagcggttg gcacagcccc agatctgcac aattgatgtc   2820
tacatggtga tggtcaagtg ttggatgatt gatgagaaca ttcgcccaac ctttaaagaa   2880
ctagccaatg agttcaccag gatggcccga gacccaccac ggtatctggt cataaagaga   2940
gagagtgggc ctggaatagc ccctgggcca gagcccatg tctgacaaa caagaagcta   3000
gaggaagtag agctggagcc agaactagac ctagacctag acttggaagc agaggaggac   3060
aacctggcaa ccaccacact gggctccgcc ctcagcctac cagttggaac acttaatcgg   3120
ccacgtggga gccagagcct tttaagtcca tcatctggat acatgcccat gaaccagggt   3180
aatcttgggg gtcttgcca ggagtctgca gtttctggga gcagtgaacg gtgccccgt   3240
ccagtctctc tacacccaat gccacgggga tgcctggcat cagagtcatc agagggcat   3300
gtaacaggct ctgaggctga gctccaggag aaagtgtcaa tgtgtagaag ccggagcagg   3360
agccggagcc cacggccacg cggagatagc gcctaccatt cccagcgcca cagtctgctg   3420
actcctgtta ccccactctc cccacccggg ttagaggaag aggatgtcaa cggttatgtc   3480
atgccagata cacacctcaa aggtactccc tcctcccggg aaggcaccct tcttcagtg   3540
ggtctcagtt ctgtcctggg tactgaagaa gaagatgaag atgaggagta tgaatacatg   3600
aaccggagga gaaggcacag tccacctcat cccctaggc caagttccct tgaggagctg   3660
ggttatgagt acatggatgt gggggtcgac ctcagtgcct ctctgggcag cacacagagt   3720
tgcccactcc accctgtacc catcatgccc actgcaggca caactccaga tgaagactat   3780
```

```
gaatatatga atcggcaacg agatggaggt ggtcctgggg gtgattatgc agccatgggg    3840
gcctgcccag catctgagca agggtatgaa gagatgagag cttttcaggg gcctggacat    3900 caggccccc atgtccatta tgcccgccta aaaactctac gtagcttaga ggctacagac    3960
tctgcctttg ataaccctga ttactggcat agcaggcttt tccccaaggc taatgccag     4020 agaacg                                                                4026
```

<210> SEQ ID NO 2
<211> LENGTH: 1342
<212> TYPE: PRT
<213> ORGANISM: Homo sapiens

<400> SEQUENCE: 2

```
Met Arg Ala Asn Asp Ala Leu Gln Val Leu Gly Leu Leu Phe Ser Leu
 1               5                  10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
```

325                     330                     335
Gly Ser Arg Phe Gln Thr Val Asp Ser Ser Asn Ile Asp Gly Phe Val
                340                     345                     350
Asn Cys Thr Lys Ile Leu Gly Asn Leu Asp Phe Leu Ile Thr Gly Leu
            355                     360                     365
Asn Gly Asp Pro Trp His Lys Ile Pro Ala Leu Asp Pro Glu Lys Leu
        370                     375                     380
Asn Val Phe Arg Thr Val Arg Glu Ile Thr Gly Tyr Leu Asn Ile Gln
385                     390                     395                     400
Ser Trp Pro Pro His Met His Asn Phe Ser Val Phe Ser Asn Leu Thr
                405                     410                     415
Thr Ile Gly Gly Arg Ser Leu Tyr Asn Arg Gly Phe Ser Leu Leu Ile
            420                     425                     430
Met Lys Asn Leu Asn Val Thr Ser Leu Gly Phe Arg Ser Leu Lys Glu
        435                     440                     445
Ile Ser Ala Gly Arg Ile Tyr Ile Ser Ala Asn Arg Gln Leu Cys Tyr
    450                     455                     460
His His Ser Leu Asn Trp Thr Lys Val Leu Arg Gly Pro Thr Glu Glu
465                     470                     475                     480
Arg Leu Asp Ile Lys His Asn Arg Pro Arg Arg Asp Cys Val Ala Glu
                485                     490                     495
Gly Lys Val Cys Asp Pro Leu Cys Ser Ser Gly Gly Cys Trp Gly Pro
            500                     505                     510
Gly Pro Gly Gln Cys Leu Ser Cys Arg Asn Tyr Ser Arg Gly Gly Val
        515                     520                     525
Cys Val Thr His Cys Asn Phe Leu Asn Gly Glu Pro Arg Glu Phe Ala
    530                     535                     540
His Glu Ala Glu Cys Phe Ser Cys His Pro Glu Cys Gln Pro Met Gly
545                     550                     555                     560
Gly Thr Ala Thr Cys Asn Gly Ser Gly Ser Asp Thr Cys Ala Gln Cys
                565                     570                     575
Ala His Phe Arg Asp Gly Pro His Cys Val Ser Ser Cys Pro His Gly
            580                     585                     590
Val Leu Gly Ala Lys Gly Pro Ile Tyr Lys Tyr Pro Asp Val Gln Asn
        595                     600                     605
Glu Cys Arg Pro Cys His Glu Asn Cys Thr Gln Gly Cys Lys Gly Pro
    610                     615                     620
Glu Leu Gln Asp Cys Leu Gly Gln Thr Leu Val Leu Ile Gly Lys Thr
625                     630                     635                     640
His Leu Thr Met Ala Leu Thr Val Ile Ala Gly Leu Val Val Ile Phe
                645                     650                     655
Met Met Leu Gly Gly Thr Phe Leu Tyr Trp Arg Gly Arg Arg Ile Gln
            660                     665                     670
Asn Lys Arg Ala Met Arg Arg Tyr Leu Glu Arg Gly Glu Ser Ile Glu
        675                     680                     685
Pro Leu Asp Pro Ser Glu Lys Ala Asn Lys Val Leu Ala Arg Ile Phe
    690                     695                     700
Lys Glu Thr Glu Leu Arg Lys Leu Lys Val Leu Gly Ser Gly Val Phe
705                     710                     715                     720
Gly Thr Val His Lys Gly Val Trp Ile Pro Glu Gly Glu Ser Ile Lys
                725                     730                     735
Ile Pro Val Cys Ile Lys Val Ile Glu Asp Lys Ser Gly Arg Gln Ser
            740                     745                     750

-continued

```
Phe Gln Ala Val Thr Asp His Met Leu Ala Ile Gly Ser Leu Asp His
        755                 760                 765
Ala His Ile Val Arg Leu Leu Gly Leu Cys Pro Gly Ser Ser Leu Gln
        770                 775                 780
Leu Val Thr Gln Tyr Leu Pro Leu Gly Ser Leu Leu Asp His Val Arg
785                 790                 795                 800
Gln His Arg Gly Ala Leu Gly Pro Gln Leu Leu Leu Asn Trp Gly Val
                805                 810                 815
Gln Ile Ala Lys Gly Met Tyr Tyr Leu Glu Glu His Gly Met Val His
            820                 825                 830
Arg Asn Leu Ala Ala Arg Asn Val Leu Leu Lys Ser Pro Ser Gln Val
            835                 840                 845
Gln Val Ala Asp Phe Gly Val Ala Asp Leu Leu Pro Pro Asp Asp Lys
    850                 855                 860
Gln Leu Leu Tyr Ser Glu Ala Lys Thr Pro Ile Lys Trp Met Ala Leu
865                 870                 875                 880
Glu Ser Ile His Phe Gly Lys Tyr Thr His Gln Ser Asp Val Trp Ser
                885                 890                 895
Tyr Gly Val Thr Val Trp Glu Leu Met Thr Phe Gly Ala Glu Pro Tyr
                900                 905                 910
Ala Gly Leu Arg Leu Ala Glu Val Pro Asp Leu Leu Glu Lys Gly Glu
            915                 920                 925
Arg Leu Ala Gln Pro Gln Ile Cys Thr Ile Asp Val Tyr Met Val Met
            930                 935                 940
Val Lys Cys Trp Met Ile Asp Glu Asn Ile Arg Pro Thr Phe Lys Glu
945                 950                 955                 960
Leu Ala Asn Glu Phe Thr Arg Met Ala Arg Asp Pro Pro Arg Tyr Leu
                965                 970                 975
Val Ile Lys Arg Glu Ser Gly Pro Gly Ile Ala Pro Gly Pro Glu Pro
            980                 985                 990
His Gly Leu Thr Asn Lys Lys Leu Glu Glu Val Glu Leu Glu Pro Glu
            995                 1000                1005
Leu Asp Leu Asp Leu Asp Leu Glu Ala Glu Glu Asp Asn Leu Ala Thr
        1010                1015                1020
Thr Thr Leu Gly Ser Ala Leu Ser Leu Pro Val Gly Thr Leu Asn Arg
1025                1030                1035                1040
Pro Arg Gly Ser Gln Ser Leu Leu Ser Pro Ser Ser Gly Tyr Met Pro
                1045                1050                1055
Met Asn Gln Gly Asn Leu Gly Gly Ser Cys Gln Glu Ser Ala Val Ser
            1060                1065                1070
Gly Ser Ser Glu Arg Cys Pro Arg Pro Val Ser Leu His Pro Met Pro
        1075                1080                1085
Arg Gly Cys Leu Ala Ser Glu Ser Ser Glu Gly His Val Thr Gly Ser
        1090                1095                1100
Glu Ala Glu Leu Gln Glu Lys Val Ser Met Cys Arg Ser Arg Ser Arg
1105                1110                1115                1120
Ser Arg Ser Pro Arg Pro Arg Gly Asp Ser Ala Tyr His Ser Gln Arg
                1125                1130                1135
His Ser Leu Leu Thr Pro Val Thr Pro Leu Ser Pro Pro Gly Leu Glu
            1140                1145                1150
Glu Glu Asp Val Asn Gly Tyr Val Met Pro Asp Thr His Leu Lys Gly
            1155                1160                1165
```

```
Thr Pro Ser Ser Arg Glu Gly Thr Leu Ser Ser Val Gly Leu Ser Ser
    1170                1175                1180

Val Leu Gly Thr Glu Glu Asp Glu Asp Glu Glu Tyr Glu Tyr Met
1185            1190                1195                1200

Asn Arg Arg Arg Arg His Ser Pro Pro His Pro Pro Arg Pro Ser Ser
                1205                1210                1215

Leu Glu Glu Leu Gly Tyr Glu Tyr Met Asp Val Gly Ser Asp Leu Ser
            1220                1225                1230

Ala Ser Leu Gly Ser Thr Gln Ser Cys Pro Leu His Pro Val Pro Ile
        1235                1240                1245

Met Pro Thr Ala Gly Thr Thr Pro Asp Glu Asp Tyr Glu Tyr Met Asn
    1250                1255                1260

Arg Gln Arg Asp Gly Gly Pro Gly Gly Asp Tyr Ala Ala Met Gly
1265            1270                1275                1280

Ala Cys Pro Ala Ser Glu Gln Gly Tyr Glu Glu Met Arg Ala Phe Gln
                1285                1290                1295

Gly Pro Gly His Gln Ala Pro His Val His Tyr Ala Arg Leu Lys Thr
            1300                1305                1310

Leu Arg Ser Leu Glu Ala Thr Asp Ser Ala Phe Asp Asn Pro Asp Tyr
        1315                1320                1325

Trp His Ser Arg Leu Phe Pro Lys Ala Asn Ala Gln Arg Thr
    1330                1335                1340

<210> SEQ ID NO 3
<211> LENGTH: 1935
<212> TYPE: DNA
<213> ORGANISM: Homo sapiens

<400> SEQUENCE: 3
atgtccgagc gcaaagaagg cagaggcaaa gggaagggca agaagaagga gcgaggctcc      60
ggcaagaagc cggagtccgc ggcgggcagc cagagcccag ccttgcctcc caattgaaa     120 gagatgaaaa gccaggaatc ggctgcaggt tccaaactag tccttcggtg tgaaaccagt     180
tctgaatact cctctctcag attcaagtgg ttcaagaatg gaatgaatt gaatcgaaaa      240 aacaaaccac aaaatatcaa gatacaaaaa agccaggga agtcagaact cgcattaac      300 aaagcatcac tggctgattc tggagagtat atgtgcaaag tgatcagcaa attaggaaat     360
gacagtgcct ctgccaatat caccatcgtg aatcaaacg agatcatcac tggtatgcca     420
gcctcaactg aaggagcata tgtgtcttca gagtctccca ttagaatatc agtatccaca     480
gaaggagcaa atacttcttc atctacatct acatccacca ctgggacaag ccatcttgta     540
aaatgtgcgg agaaggagaa aactttctgt gtgaatggag gggagtgctt catggtgaaa     600
gacctttcaa acccctcgag atacttgtgc aagtgcccaa atgagtttac tggtgatcgc     660
tgccaaaact acgtaatggc cagcttctac aagcatcttg ggattgaatt tatgaggcg      720 gaggagctgt accagaagag agtgctgacc ataaccggca tctgcatcgc cctccttgtg     780
gtcggcatca tgtgtgtggt ggcctactgc aaaaccaaga acagcggaaa aagctgcat      840 gaccgtcttc ggcagagcct tcggtctgaa cgaaacaata tgatgaacat tgccaatggg     900
cctcaccatc ctaacccacc ccccgagaat gtccagctgg tgaatcaata cgtatctaaa     960
aacgtcatct ccagtgagca tattgttgag agagaagcag agacatcctt ttccaccagt    1020
cactatactt ccacagcccca tcactccact actgtcaccc agactcctag ccacagctgg    1080
agcaacggac acactgaaag catcctttcc gaaagccact ctgtaatcgt gatgtcatcc    1140
```

-continued

```
gtagaaaaca gtaggcacag cagcccaact gggggcccaa gaggacgtct taatggcaca    1200
ggaggccctc gtgaatgtaa cagcttcctc aggcatgcca gagaaacccc tgattcctac    1260
cgagactctc ctcatagtga aaggtatgtg tcagccatga ccaccccggc tcgtatgtca    1320
cctgtagatt tccacacgcc aagctccccc aaatcgcccc cttcggaaat gtctccaccc    1380
gtgtccagca tgacggtgtc catgccttcc atggcggtca gccccttcat ggaagaagag    1440
agacctctac ttctcgtgac accaccaagg ctgcgggaga agaagtttga ccatcaccct    1500
cagcagttca gctccttcca ccacaacccc gcgcatgaca gtaacagcct ccctgctagc    1560
cccttgagga tagtggagga tgaggagtat gaaacgaccc aagagtacga gccagcccaa    1620
gagcctgtta agaaactcgc aatagccgg cgggccaaaa gaaccaagcc caatggccac    1680
attgctaaca gattggaagt ggacagcaac acaagctccc agagcagtaa ctcagagagt    1740
gaaacagaag atgaaagagt aggtgaagat acgcctttcc tgggcataca gaaccccctg    1800
gcagccagtc ttgaggcaac acctgccttc cgcctggctg acagcaggac taacccagca    1860
ggccgcttct cgacacagga agaaatccag gccaggctgt ctagtgtaat tgctaaccaa    1920
gaccctattg ctgta                                                     1935
```

<210> SEQ ID NO 4
<211> LENGTH: 645
<212> TYPE: PRT
<213> ORGANISM: Homo sapiens

<400> SEQUENCE: 4

```
Met Ser Glu Arg Lys Glu Gly Arg Gly Lys Gly Lys Gly Lys Lys Lys
 1               5                  10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Glu Ile Ile Thr Gly Met Pro Ala Ser Thr Glu
    130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Ser Thr Thr Gly Thr
                165                 170                 175

Ser His Leu Val Lys Cys Ala Glu Lys Glu Lys Thr Phe Cys Val Asn
            180                 185                 190

Gly Gly Glu Cys Phe Met Val Lys Asp Leu Ser Asn Pro Ser Arg Tyr
        195                 200                 205

Leu Cys Lys Cys Pro Asn Glu Phe Thr Gly Asp Arg Cys Gln Asn Tyr
    210                 215                 220

Val Met Ala Ser Phe Tyr Lys His Leu Gly Ile Glu Phe Met Glu Ala
```

-continued

```
            225                 230                 235                 240

Glu Glu Leu Tyr Gln Lys Arg Val Leu Thr Ile Thr Gly Ile Cys Ile
                245                 250                 255

Ala Leu Leu Val Val Gly Ile Met Cys Val Val Ala Tyr Cys Lys Thr
                260                 265                 270

Lys Lys Gln Arg Lys Lys Leu His Asp Arg Leu Arg Gln Ser Leu Arg
            275                 280                 285

Ser Glu Arg Asn Asn Met Met Asn Ile Ala Asn Gly Pro His His Pro
        290                 295                 300

Asn Pro Pro Pro Glu Asn Val Gln Leu Val Asn Gln Tyr Val Ser Lys
305                 310                 315                 320

Asn Val Ile Ser Ser Glu His Ile Val Glu Arg Glu Ala Glu Thr Ser
                325                 330                 335

Phe Ser Thr Ser His Tyr Thr Ser Thr Ala His His Ser Thr Thr Val
                340                 345                 350

Thr Gln Thr Pro Ser His Ser Trp Ser Asn Gly His Thr Glu Ser Ile
            355                 360                 365

Leu Ser Glu Ser His Ser Val Ile Val Met Ser Ser Val Glu Asn Ser
        370                 375                 380

Arg His Ser Ser Pro Thr Gly Gly Pro Arg Gly Arg Leu Asn Gly Thr
385                 390                 395                 400

Gly Gly Pro Arg Glu Cys Asn Ser Phe Leu Arg His Ala Arg Glu Thr
                405                 410                 415

Pro Asp Ser Tyr Arg Asp Ser Pro His Ser Glu Arg Tyr Val Ser Ala
            420                 425                 430

Met Thr Thr Pro Ala Arg Met Ser Pro Val Asp Phe His Thr Pro Ser
        435                 440                 445

Ser Pro Lys Ser Pro Ser Glu Met Ser Pro Pro Val Ser Ser Met
        450                 455                 460

Thr Val Ser Met Pro Ser Met Ala Val Ser Pro Phe Met Glu Glu Glu
465                 470                 475                 480

Arg Pro Leu Leu Leu Val Thr Pro Pro Arg Leu Arg Glu Lys Lys Phe
                485                 490                 495

Asp His His Pro Gln Gln Phe Ser Ser Phe His His Asn Pro Ala His
            500                 505                 510

Asp Ser Asn Ser Leu Pro Ala Ser Pro Leu Arg Ile Val Glu Asp Glu
        515                 520                 525

Glu Tyr Glu Thr Thr Gln Glu Tyr Glu Pro Ala Gln Glu Pro Val Lys
        530                 535                 540

Lys Leu Ala Asn Ser Arg Arg Ala Lys Arg Thr Lys Pro Asn Gly His
545                 550                 555                 560

Ile Ala Asn Arg Leu Glu Val Asp Ser Asn Thr Ser Ser Gln Ser Ser
                565                 570                 575

Asn Ser Glu Ser Glu Thr Glu Asp Glu Arg Val Gly Glu Asp Thr Pro
            580                 585                 590

Phe Leu Gly Ile Gln Asn Pro Leu Ala Ala Ser Leu Glu Ala Thr Pro
        595                 600                 605

Ala Phe Arg Leu Ala Asp Ser Arg Thr Asn Pro Ala Gly Arg Phe Ser
        610                 615                 620

Thr Gln Glu Glu Ile Gln Ala Arg Leu Ser Ser Val Ile Ala Asn Gln
625                 630                 635                 640

Asp Pro Ile Ala Val
            645
```

<210> SEQ ID NO 5
<211> LENGTH: 3765
<212> TYPE: DNA
<213> ORGANISM: Homo sapiens

<400> SEQUENCE: 5

| | | | | | |
|---|---|---|---|---|---|
| atggagctgg | cggccttgtg | ccgctggggg | ctcctcctcg | ccctcttgcc | ccccggagcc | 60 |
| gcgagcaccc | aagtgtgcac | cggcacagac | atgaagctgc | ggctccctgc | cagtcccgag | 120 |
| acccacctgg | acatgctccg | ccacctctac | cagggctgcc | aggtggtgca | gggaaacctg | 180 |
| gaactcacct | acctgcccac | caatgccagc | ctgtccttcc | tgcaggatat | ccaggaggtg | 240 |
| cagggctacg | tgctcatcgc | tcacaaccaa | gtgaggcagg | tcccactgca | gaggctgcgg | 300 |
| attgtgcgag | gcacccagct | cttgaggac | aactatgccc | tggccgtgct | agacaatgga | 360 |
| gacccgctga | caataccac | ccctgtcaca | ggggcctccc | caggaggcct | gcggagctg | 420 |
| cagcttcgaa | gcctcacaga | gatcttgaaa | ggaggggtct | tgatccagcg | gaaccccag | 480 |
| ctctgctacc | aggacacgat | tttgtggaag | gacatcttcc | acaagaacaa | ccagctggct | 540 |
| ctcacactga | tagacaccaa | ccgctctcgg | gcctgccacc | cctgttctcc | gatgtgtaag | 600 |
| ggctcccgct | gctgggggaga | gagttctgag | gattgtcaga | gcctgacgcg | cactgtctgt | 660 |
| gccggtggct | gtgcccgctg | caaggggcca | ctgcccactg | actgctgcca | tgagcagtgt | 720 |
| gctgccggct | gcacgggccc | caagcactct | gactgcctgg | cctgcctcca | cttcaaccac | 780 |
| agtggcatct | gtgagctgca | ctgcccagcc | ctggtcacct | acaacacaga | cacgtttgag | 840 |
| tccatgccca | atcccgaggg | ccggtataca | ttcggcgcca | gctgtgtgac | tgcctgtccc | 900 |
| tacaactacc | tttctacgga | cgtgggatcc | tgcaccctcg | tctgccccct | gcacaaccaa | 960 |
| gaggtgacag | cagaggatgg | aacacagcgg | tgtgagaagt | gcagcaagcc | ctgtgcccga | 1020 |
| gtgtgctatg | gtctgggcat | ggagcacttg | cgagaggtga | gggcagttac | cagtgccaat | 1080 |
| atccaggagt | ttgctggctg | caagaagatc | tttgggagcc | tggcatttct | gccggagagc | 1140 |
| tttgatgggg | acccagcctc | caacactgcc | ccgctccagc | cagagcagct | ccaagtgttt | 1200 |
| gagactctgg | aagagatcac | aggttaccta | tacatctcag | catggccgga | cagcctgcct | 1260 |
| gacctcagcg | tcttccagaa | cctgcaagta | atccggggac | gaattctgca | caatggcgcc | 1320 |
| tactcgctga | ccctgcaagg | gctgggcatc | agctggctgg | ggctgcgctc | actgagggaa | 1380 |
| ctgggcagtg | gactggccct | catccaccat | aacacccacc | tctgcttcgt | gcacacggtg | 1440 |
| ccctgggacc | agctctttcg | gaacccgcac | caagctctgc | tccacactgc | caaccggcca | 1500 |
| gaggacgagt | gtgtgggcga | gggcctggcc | tgccaccagc | tgtgcgcccg | agggcactgc | 1560 |
| tggggtccag | ggcccaccca | gtgtgtcaac | tgcagccagt | ccttcggg | ccaggagtgc | 1620 |
| gtggaggaat | gccgagtact | gcaggggctc | ccaggggagt | atgtgaatgc | caggcactgt | 1680 |
| ttgccgtgcc | accctgagtg | tcagccccag | aatggctcag | tgacctgttt | tggaccggag | 1740 |
| gctgaccagt | gtgtggcctg | tgcccactat | aaggaccctc | ccttctgcgt | ggcccgctgc | 1800 |
| cccagcggtg | tgaaacctga | cctctcctac | atgcccatct | ggaagtttcc | agatgaggag | 1860 |
| ggcgcatgcc | agccttgccc | catcaactgc | acccactcct | gtgtggacct | ggatgacaag | 1920 |
| ggctgccccg | ccgagcagag | agccagccct | ctgacgtcca | tcgtctctgc | ggtggttggc | 1980 |
| attctgctgg | tcgtggtctt | ggggtggtc | tttgggatcc | tcatcaagcg | acggcagcag | 2040 |
| aagatccgga | agtacacgat | gcggagactg | ctgcaggaaa | cggagctggt | ggagccgctg | 2100 |

```
acacctagcg agcgatgcc caaccaggcg cagatgcgga tcctgaaaga dacggagctg   2160
aggaaggtga aggtgcttgg atctggcgct tttggcacag tctacaaggg catctggatc   2220
cctgatgggg agaatgtgaa aattccagtg gccatcaaag tgttgaggga aaacacatcc   2280
cccaaagcca acaaagaaat cttagacgaa gcatacgtga tggctggtgt gggctcccca   2340
tatgtctccc gccttctggg catctgcctg acatccacgg tgcagctggt gacacagctt   2400
atgccctatg gctgcctctt agaccatgtc cgggaaaacc gcggacgcct gggctcccag   2460
gacctgctga actggtgtat gcagattgcc aaggggatga gctacctgga ggatgtgcgg   2520
ctcgtacaca gggacttggc cgctcggaac gtgctggtca gagtcccaa ccatgtcaaa   2580 attacagact cgggctggc tcggctgctg acattgacg agacagagta ccatgcagat   2640
gggggcaagt gcccatcaa gtggatggcg ctggagtcca ttctccgccg gcggttcacc   2700
caccagagtg atgtgtggag ttatggtgtg actgtgtggg agctgatgac ttttggggcc   2760
aaaccttacg atgggatccc agcccggag atccctgacc tgctggaaaa ggggagcgg   2820 ctgccccagc ccccatctg caccattgat gtctacatga tcatggtcaa atgttggatg   2880
attgactctg aatgtcggcc aagattccgg gagttggtgt ctgaattctc ccgcatggcc   2940
agggaccccc agcgctttgt ggtcatccag aatgaggact gggcccagc cagtcccttg   3000 gacagcacct tctaccgctc actgctggag gacgatgaca tggggacct ggtgatgct   3060 gaggagtatc tggtacccca gcagggcttc ttctgtccag accctgcccc gggcgctggg   3120
ggcatggtcc accacaggca ccgcagctca tctaccagga gtggcggtgg ggacctgaca   3180
ctagggctgg agccctctga agaggaggcc cccaggtctc cactggcacc ctccgaaggg   3240
gctggctccg atgtatttga tggtgacctg ggaatggggg cagccaaggg gctgcaaagc   3300
ctccccacac atgaccccag ccctctacag cggtacagtg aggaccccac agtacccctg   3360
ccctctgaga ctgatggcta cgttgccccc ctgacctgca gccccagcc tgaatatgtg   3420 aaccagccag atgttcggcc ccagcccccct tcgccccgag agggccctct gcctgctgcc   3480
cgacctgctg gtgccactct ggaaagggcc aagactctct ccccagggaa gaatggggtc   3540
gtcaaagacg ttttgccttt tggggtgcc gtggagaacc ccgagtactt gacaccccag   3600
ggaggagctg cccctcagcc ccaccctcct cctgccttca gcccagcctt cgacaacctc   3660
tattactggg accaggaccc accagagcgg ggggctccac ccagcacctt caaagggaca   3720
cctacggcag agaacccaga gtacctgggt ctggacgtgc cagtg              3765
```

<210> SEQ ID NO 6
<211> LENGTH: 1255
<212> TYPE: PRT
<213> ORGANISM: Homo sapiens

<400> SEQUENCE: 6

```
Met Glu Leu Ala Ala Leu Cys Arg Trp Gly Leu Leu Leu Ala Leu Leu
 1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80
```

-continued

```
Gln Gly Tyr Val Leu Ile Ala His Asn Gln Val Arg Gln Val Pro Leu
                85                  90                  95
Gln Arg Leu Arg Ile Val Arg Gly Thr Gln Leu Phe Glu Asp Asn Tyr
            100                 105                 110
Ala Leu Ala Val Leu Asp Asn Gly Asp Pro Leu Asn Asn Thr Thr Pro
            115                 120                 125
Val Thr Gly Ala Ser Pro Gly Gly Leu Arg Glu Leu Gln Leu Arg Ser
130                 135                 140
Leu Thr Glu Ile Leu Lys Gly Gly Val Leu Ile Gln Arg Asn Pro Gln
145                 150                 155                 160
Leu Cys Tyr Gln Asp Thr Ile Leu Trp Lys Asp Ile Phe His Lys Asn
                165                 170                 175
Asn Gln Leu Ala Leu Thr Leu Ile Asp Thr Asn Arg Ser Arg Ala Cys
            180                 185                 190
His Pro Cys Ser Pro Met Cys Lys Gly Ser Arg Cys Trp Gly Glu Ser
            195                 200                 205
Ser Glu Asp Cys Gln Ser Leu Thr Arg Thr Val Cys Ala Gly Gly Cys
210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
                245                 250                 255
His Phe Asn His Ser Gly Ile Cys Glu Leu His Cys Pro Ala Leu Val
            260                 265                 270
Thr Tyr Asn Thr Asp Thr Phe Glu Ser Met Pro Asn Pro Glu Gly Arg
            275                 280                 285
Tyr Thr Phe Gly Ala Ser Cys Val Thr Ala Cys Pro Tyr Asn Tyr Leu
290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Glu
            340                 345                 350
Val Arg Ala Val Thr Ser Ala Asn Ile Gln Glu Phe Ala Gly Cys Lys
            355                 360                 365
Lys Ile Phe Gly Ser Leu Ala Phe Leu Pro Glu Ser Phe Asp Gly Asp
            370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
            420                 425                 430
Gly Arg Ile Leu His Asn Gly Ala Tyr Ser Leu Thr Leu Gln Gly Leu
        435                 440                 445
Gly Ile Ser Trp Leu Gly Leu Arg Ser Leu Arg Leu Gly Ser Gly
        450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
```

-continued

```
                500                 505                 510
Gln Leu Cys Ala Arg Gly His Cys Trp Gly Pro Gly Pro Thr Gln Cys
            515                 520                 525
Val Asn Cys Ser Gln Phe Leu Arg Gly Gln Glu Cys Val Glu Glu Cys
            530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                        565                 570                 575
Phe Gly Pro Glu Ala Asp Gln Cys Val Ala Cys Ala His Tyr Lys Asp
                580                 585                 590
Pro Pro Phe Cys Val Ala Arg Cys Pro Ser Gly Val Lys Pro Asp Leu
                595                 600                 605
Ser Tyr Met Pro Ile Trp Lys Phe Pro Asp Glu Glu Gly Ala Cys Gln
            610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser Ile Val Ser
                    645                 650                 655
Ala Val Val Gly Ile Leu Leu Val Val Val Leu Gly Val Val Phe Gly
                660                 665                 670
Ile Leu Ile Lys Arg Arg Gln Gln Lys Ile Arg Lys Tyr Thr Met Arg
            675                 680                 685
Arg Leu Leu Gln Glu Thr Glu Leu Val Glu Pro Leu Thr Pro Ser Gly
            690                 695                 700
Ala Met Pro Asn Gln Ala Gln Met Arg Ile Leu Lys Glu Thr Glu Leu
705                 710                 715                 720
Arg Lys Val Lys Val Leu Gly Ser Gly Ala Phe Gly Thr Val Tyr Lys
                    725                 730                 735
Gly Ile Trp Ile Pro Asp Gly Glu Asn Val Lys Ile Pro Val Ala Ile
                740                 745                 750
Lys Val Leu Arg Glu Asn Thr Ser Pro Lys Ala Asn Lys Glu Ile Leu
            755                 760                 765
Asp Glu Ala Tyr Val Met Ala Gly Val Gly Ser Pro Tyr Val Ser Arg
770                 775                 780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
                805                 810                 815
Leu Gly Ser Gln Asp Leu Leu Asn Trp Cys Met Gln Ile Ala Lys Gly
                820                 825                 830
Met Ser Tyr Leu Glu Asp Val Arg Leu Val His Arg Asp Leu Ala Ala
            835                 840                 845
Arg Asn Val Leu Val Lys Ser Pro Asn His Val Lys Ile Thr Asp Phe
            850                 855                 860
Gly Leu Ala Arg Leu Leu Asp Ile Asp Glu Thr Glu Tyr His Ala Asp
865                 870                 875                 880
Gly Gly Lys Val Pro Ile Lys Trp Met Ala Leu Glu Ser Ile Leu Arg
                    885                 890                 895
Arg Arg Phe Thr His Gln Ser Asp Val Trp Ser Tyr Gly Val Thr Val
                900                 905                 910
Trp Glu Leu Met Thr Phe Gly Ala Lys Pro Tyr Asp Gly Ile Pro Ala
            915                 920                 925
```

-continued

```
Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr Leu
    1010                1015                1020

Val Pro Gln Gln Gly Phe Phe Cys Pro Asp Pro Ala Pro Gly Ala Gly
1025                1030                1035                1040

Gly Met Val His His Arg His Arg Ser Ser Ser Thr Arg Ser Gly Gly
                1045                1050                1055

Gly Asp Leu Thr Leu Gly Leu Glu Pro Ser Glu Glu Glu Ala Pro Arg
            1060                1065                1070

Ser Pro Leu Ala Pro Ser Glu Gly Ala Gly Ser Asp Val Phe Asp Gly
        1075                1080                1085

Asp Leu Gly Met Gly Ala Ala Lys Gly Leu Gln Ser Leu Pro Thr His
    1090                1095                1100

Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
                1125                1130                1135

Pro Glu Tyr Val Asn Gln Pro Asp Val Arg Pro Gln Pro Pro Ser Pro
            1140                1145                1150

Arg Glu Gly Pro Leu Pro Ala Ala Arg Pro Ala Gly Ala Thr Leu Glu
        1155                1160                1165

Arg Ala Lys Thr Leu Ser Pro Gly Lys Asn Gly Val Val Lys Asp Val
    1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Ala Phe Ser Pro Ala
                1205                1210                1215

Phe Asp Asn Leu Tyr Tyr Trp Asp Gln Asp Pro Pro Glu Arg Gly Ala
            1220                1225                1230

Pro Pro Ser Thr Phe Lys Gly Thr Pro Thr Ala Glu Asn Pro Glu Tyr
        1235                1240                1245

Leu Gly Leu Asp Val Pro Val
    1250                1255

<210> SEQ ID NO 7
<211> LENGTH: 43
<212> TYPE: DNA
<213> ORGANISM: Artificial Sequence
<220> FEATURE:
<223> OTHER INFORMATION: random library oligonucleotide

<400> SEQUENCE: 7
gggugccagc gaaaguugcg uaugggucac aucgcaggca ccc                    43

<210> SEQ ID NO 8
<211> LENGTH: 49
```

<212> TYPE: DNA
<213> ORGANISM: Artificial Sequence
<220> FEATURE:
<223> OTHER INFORMATION: random library oligonucleotide

<400> SEQUENCE: 8
agaacaaucg cauaggccgc aagguuaguu ucguuguccg cccggugca                49

<210> SEQ ID NO 9
<211> LENGTH: 49
<212> TYPE: DNA
<213> ORGANISM: Artificial Sequence
<220> FEATURE:
<223> OTHER INFORMATION: random library oligonucleotide

<400> SEQUENCE: 9
acgaguauag cccacauggc acgacaggga cguucaugu gcacaguug                 49

<210> SEQ ID NO 10
<211> LENGTH: 49
<212> TYPE: DNA
<213> ORGANISM: Artificial Sequence
<220> FEATURE:
<223> OTHER INFORMATION: random library oligonucleotide

<400> SEQUENCE: 10
agaucaggac agagcgcaca ggugccaucc uggucuaacg cccucgaug                49

<210> SEQ ID NO 11
<211> LENGTH: 49
<212> TYPE: DNA
<213> ORGANISM: Artificial Sequence
<220> FEATURE:
<223> OTHER INFORMATION: random library oligonucleotide

<400> SEQUENCE: 11
gaggggcgag gacgccgagu auagccccua gagguggaug uuucacggu                49

<210> SEQ ID NO 12
<211> LENGTH: 49
<212> TYPE: DNA
<213> ORGANISM: Artificial Sequence
<220> FEATURE:
<223> OTHER INFORMATION: random library oligonucleotide

<400> SEQUENCE: 12
cagcgaaagu ugcguauggg ucacaucgca ggcacauguc aucgggcg                 49

<210> SEQ ID NO 13
<211> LENGTH: 49
<212> TYPE: DNA
<213> ORGANISM: Artificial Sequence
<220> FEATURE:
<223> OTHER INFORMATION: random library oligonucleotide

<400> SEQUENCE: 13
uugagagguc gugccaacuc ucaagguugu cuuugcucuc cgcucugug                49

<210> SEQ ID NO 14
<211> LENGTH: 100
<212> TYPE: DNA
<213> ORGANISM: Artificial Sequence
<220> FEATURE:
<223> OTHER INFORMATION: random library oligonucleotide
<220> FEATURE:
<221> NAME/KEY: misc_feature
<222> LOCATION: (35)...(83)

```
<223> OTHER INFORMATION: n = a, t, c, or g

<400> SEQUENCE: 14
taatacgact cactataggg aattccgcgt gtgcnnnnnn nnnnnnnnnn nnnnnnnnnn      60
nnnnnnnnnn nnnnnnnnnn nnngtccgtt cgggatcctc                          100

<210> SEQ ID NO 15
<211> LENGTH: 100
<212> TYPE: DNA
<213> ORGANISM: Artificial Sequence
<220> FEATURE:
<223> OTHER INFORMATION: random library oligonucleotide

<400> SEQUENCE: 15
taatacgact cactataggg aattccgcgt gtgccagcga aaguugcgua ugggucacau      60
cgcaggcaca ugucaucugg gcggtccgtt cgggatcctc                          100

<210> SEQ ID NO 16
<211> LENGTH: 78
<212> TYPE: DNA
<213> ORGANISM: Artificial Sequence
<220> FEATURE:
<223> OTHER INFORMATION: random library oligonucleotide

<400> SEQUENCE: 16
ggaauuccgc gugugccagc gaaaguugcg uaugggucac aucgcaggca caugucaucu      60
gggcgguccg uucgggau                                                   78

<210> SEQ ID NO 17
<211> LENGTH: 50
<212> TYPE: DNA
<213> ORGANISM: Artificial Sequence
<220> FEATURE:
<223> OTHER INFORMATION: random library oligonucleotide

<400> SEQUENCE: 17
cagcgaaagu ugcguauggg ucacaucgca ggcacauguc aucgggcgg                 50

<210> SEQ ID NO 18
<211> LENGTH: 35
<212> TYPE: DNA
<213> ORGANISM: Artificial Sequence
<220> FEATURE:
<223> OTHER INFORMATION: random library oligonucleotide

<400> SEQUENCE: 18
cagcgaaagu ugcguauggg ucacaucgca ggcac                                35

<210> SEQ ID NO 19
<211> LENGTH: 31
<212> TYPE: DNA
<213> ORGANISM: Artificial Sequence
<220> FEATURE:
<223> OTHER INFORMATION: random library oligonucleotide

<400> SEQUENCE: 19
cagcgaaagu ugcguauggg ucacaucgca g                                  31

<210> SEQ ID NO 20
<211> LENGTH: 100
<212> TYPE: DNA
<213> ORGANISM: Artificial Sequence
<220> FEATURE:
<223> OTHER INFORMATION: random library oligonucleotide
```

```
<400> SEQUENCE: 20
taatacgact cactataggg aattccgcgt gtgcagaaca atcgcatagg ccgcaaggtt        60
agtttcgttg tccgcccggt gcagtccgtt cgggatcctc                             100
```